(12) United States Patent
Elomari

(10) Patent No.: US 6,616,911 B2
(45) Date of Patent: *Sep. 9, 2003

(54) PROCESS FOR PREPARING ZEOLITES USING PYRROLIDINIUM CATIONS

(75) Inventor: Saleh Elomari, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/905,460

(22) Filed: Jul. 13, 2001

(65) Prior Publication Data

US 2002/0081262 A1 Jun. 27, 2002

Related U.S. Application Data

(63) Continuation-in-part of application No. 09/520,640, filed on Mar. 7, 2000, now Pat. No. 6,475,463.

(51) Int. Cl.$^7$ .......................... C01B 39/04; C01B 39/36
(52) U.S. Cl. ...................... 423/706; 423/DIG. 27; 423/DIG. 29
(58) Field of Search ................. 423/706, DIG. 27, 423/DIG. 29

(56) References Cited

U.S. PATENT DOCUMENTS

| | | | |
|---|---|---|---|
| 3,308,069 A | 3/1967 | Wadlinger et al. | |
| 3,709,979 A | 1/1973 | Chu | |
| 3,832,449 A | 8/1974 | Rosinski et al. | |
| 4,021,447 A | 5/1977 | Rubin et al. | |
| 4,259,306 A | * 3/1981 | Pelrine | 423/326 |
| 4,391,785 A | * 7/1983 | Rosinski et al. | 423/332 |
| 4,941,963 A | 7/1990 | Valyocsik | |
| 5,254,514 A | 10/1993 | Nakagawa | |
| 5,707,600 A | 1/1998 | Nakagawa et al. | |

OTHER PUBLICATIONS

U.S. patent application Ser. No. 09/520,640, Elomari et al.
U.S. patent application Ser. No. 09/905,404, Elomari.
U.S. patent application Ser. No. 09/905,456, Elomari.
U.S. patent application Ser. No. 09/905,472, Elomari.
Szostak, Handbook of Molecular Sieves, Van Nostrand Reinhold, 1992, pp. 532–533.
Szostak, Handbook of Molecular Sieves, Van Nostrand Reinhold, 1992, pp. 92–97.
Szostak, Handbook of Molecular Sieves, Van Nostrand Reinhold, 1992, pp. 530–531.

* cited by examiner

Primary Examiner—David Sample
(74) Attorney, Agent, or Firm—Richard J. Sheridan

(57) ABSTRACT

The present invention relates to a process for preparing zeolites using pyrrolidinium cations as structure directing agents.

57 Claims, No Drawings

PROCESS FOR PREPARING ZEOLITES USING PYRROLIDINIUM CATIONS

This application is a continuation-in-part of application Ser. No. 09/520,640, filed Mar. 7, 2000 U.S. Pat. No. 6,475,463.

BACKGROUND OF THE INVENTION

1. Field of the Invention

The present invention relates to a process for preparing medium pore size zeolites using pyrrolidinium cations as structure directing agents (SDA's).

2. State of the Art

It has now been found that zeolites can be prepared using pyrrolidinium cations as structure directing agents.

SUMMARY OF THE INVENTION

In accordance with the present invention, there is provided a process for preparing a medium pore size zeolite which comprises:

(a) preparing an aqueous solution from (1) sources of an alkali metal oxide, alkaline earth metal oxide or mixtures thereof, (2) sources of an oxide selected from oxides of silicon, germanium or mixtures thereof; (3) sources of an oxide selected from the oxides of aluminum, boron, iron, gallium, indium, titanium, vanadium or mixtures thereof; and (4) at least one pyrrolidinium cation capable of forming the zeolite having the formula

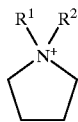

(I)

where $R^1$ is $C_1$–$C_4$ alkyl or benzyl, and $R^2$ is $C_5$–$C_8$ cycloalkyl, or alkylated $C_5$–$C_8$ cycloalkyl;

(b) maintaining the aqueous solution under conditions sufficient to form crystals of the zeolite; and (c) recovering the crystals of the zeolite.

The present invention also provides this process further comprising replacing alkali and/or alkaline earth metal cations of the recovered zeolite, at least in part, by ion exchange with a cation or mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

The present invention also provides a zeolite composition, as-synthesized and in the anhydrous state, whose general composition, in terms of mole ratios, is as follows:

$YO_2/W_cO_d \geq 20$ $Q/YO_2$ 0.02–0.10

$M_{2/n}/YO_2$ 0.01–0.10 wherein Y is silicon, germanium or a mixture thereof; W is aluminum, boron, gallium, indium, iron, titanium, vanadium or mixtures thereof; c is 1 or 2; d is 2 when c is 1 (i.e., W is tetravalent) or d is 3 or 5 when c is 2 (i.e., d is 3 when W is trivalent or 5 when W is pentavalent); Q is at least one pyrrolidinium cation capable of forming the zeolite and having formula (I) above; M is an alkali metal cation, alkaline earth metal cation or mixtures thereof; and n is the valence of M (i.e., 1 or 2).

DETAILED DESCRIPTION OF PREFERRED EMBODIMENTS

The present invention comprises:

(a) preparing an aqueous solution from sources of oxides capable of forming a zeolite and at least one pyrrolidinium cation capable of forming the zeolite and having formula (I) above;

(b) maintaining the aqueous solution under conditions sufficient to form crystals of the zeolite; and (c) recovering the crystals of the zeolite.

While not wishing to be bound or limited by any theory, it is believed that the pyrrolidinium cations of this invention act as a structure directing agent or templating agent in the reaction which forms the zeolite.

The process of the present invention comprises forming a reaction mixture from sources of alkali and/or alkaline earth metal (M) cations with valences n (i.e., 1 or 2); sources of an oxide of aluminum, boron, iron, gallium, indium, titanium, vanadium or mixtures thereof (W); sources of an oxide of silicon, germanium or mixtures thereof (Y); at least one pyrrolidinium cation of this invention (Q); and water, said reaction mixture having a composition in terms of mole ratios within the following ranges:

| Reactants | General | Preferred |
|---|---|---|
| $YO_2/W_aO_b$ | 20–∞ | 25–90 |
| $OH^-/YO_2$ | 0.10–0.50 | 0.15–0.30 |
| $Q/YO_2$ | 0.05–0.50 | 0.10–0.30 |
| $M_{2/n}/YO_2$ | 0.02–0.40 | 0.01–0.30 |
| $H_2O/YO_2$ | 10–100 | 25–50 |

Where Y, W, Q, M and n are as defined above, and a is 1 or 2, and b is 2 when a is 1 (i.e., W is tetravalent) and b is 3 when a is 2 (i.e., W is trivalent).

Typical sources of aluminum oxide for the reaction mixture include aluminates, alumina, hydrated aluminum hydroxides, and aluminum compounds such as $AlCl_3$ and $Al_2(SO_4)_3$. Typical sources of silicon oxide include silica hydrogel, silicic acid, colloidal silica, tetraalkyl orthosilicates, silica hydroxides, and fumed silicas. Gallium, iron, boron, indium, titanium, vanadium and germanium can be added in forms corresponding to their aluminum and silicon counterparts. Trivalent elements stabilized on silica colloids are also useful reagents.

The pyrrolidinium cations useful in the practice of this invention are those which are capable of forming a zeolite. The pyrrolidinium cations of this invention are represented by the following formula:

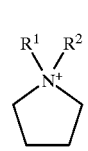

(I)

where $R^1$ is $C_1$–$C_4$ alkyl (e.g., methyl, ethyl, propyl, butyl or isobutyl) or benzyl, and $R^2$ is $C_5$–$C_8$ cycloalkyl (e.g., cyclopentyl, cyclohexyl, or cyclooctyl), or alkylated $C_5$–$C_8$ cycloalkyl (e.g., 2,4,4-trimethylcyclopentyl or 3,3,5-trimethylcyclohexyl).

In preparing the zeolites in accordance with the present invention, the reactants and the pyrrolidinium cation are dissolved in water and the resulting reaction mixture is maintained at an elevated temperature until crystals are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

The hydrothermal crystallization is usually conducted under pressure and usually in an autoclave so that the reaction mixture is subject to autogenous pressure. The reaction mixture should be stirred during crystallization.

Once the crystals have formed, the solid product is separated from the reaction mixture by standard mechanical separation techniques, such as filtration. The crystals are water-washed and then dried, e.g., at 90° C. to 150° C. for from 8 to 24 hours, to obtain the as-synthesized zeolite crystals. The drying step can be performed at atmospheric or subatmospheric pressures.

During the hydrothermal crystallization step, the crystals can be allowed to nucleate spontaneously from the reaction mixture. The reaction mixture can also be seeded with crystals of the desired zeolite both to direct, and accelerate the crystallization, as well as to minimize the formation of any undesired crystalline phases. When seed crystals are used, typically about 0.5% to about 5.0% by weight (based on the weight of silica used in the reaction mixture) of the seed crystals are added.

Due to the unpredictability of the factors which control nucleation and crystallization in the art of crystalline oxide synthesis, not every combination of reagents, reactant ratios, and reaction conditions will result in crystalline products. Selecting crystallization conditions which are effective for producing crystals may require routine modifications to the reaction mixture or to the reaction conditions, such as temperature, and/or crystallization time. Making these modifications are well within the capabilities of one skilled in the art.

The zeolite product made by the process of this invention has an as-synthesized composition comprising, in terms of mole ratios in the anhydrous state, the following:

$YO_2/W_cO_d \geq 20$ $Q/YO_2$ 0.02–0.10

$M_{2/n}/YO_2$ 0.01–0.10 wherein Y, W, c, d, Q, M and n are as defined above. Preferably, Y is silicon, W is aluminum, and M is sodium.

The zeolite products made in accordance with this invention were identified by their X-ray diffraction (XRD) pattern. The X-ray powder diffraction patterns were determined by standard techniques. The radiation was the K-alpha/doublet of copper. In the X-ray data shown below, the peak heights I and the positions, as a function of 2 theta where theta is the Bragg angle, were read from the relative intensities, $100 \times I/I_o$ where $I_o$ is the intensity of the strongest line or peak, and d, the interplanar spacing in Angstroms corresponding to the recorded lines, can be calculated.

The pyrrolidinium SDA's of this invention can be used to prepare a variety of medium pore zeolites, including beta zeolite, ZSM-11, ZSM-12, SSZ-37, SSZ-55, SSZ-57, SSZ-58, and SSZ-60. Table A below shows the zeolites that have been made using the pyrrolidinium cations of this invention, as well as the particular cations that can be used to make each zeolite. It should be noted that in Table A, "Me" represents a methyl group and the positive charge on the nitrogen atom is not shown.

TABLE A

| Structure | Zeolite |
|---|---|
| N-methyl-N-cyclopentylpyrrolidinium | ZSM-12 |
| N-(cyclopentylmethyl)pyrrolidinium with methyl | SSZ-37 |
| N-cyclopentyl-N-(4-methylbutyl)pyrrolidinium | ZSM-11 |
| N-cyclopentyl-N-(2-methylpropyl)pyrrolidinium (with Me substituent) | SSZ-55 |
| N-(2,2,4-trimethylcyclopentyl)-N-methylpyrrolidinium | SSZ-60 |
| N-methyl-N-cyclohexylpyrrolidinium | ZSM-12 |
| N-ethyl-N-cyclohexylpyrrolidinium | ZSM-12 |
| N-cyclohexyl-N-(2-methylethyl)pyrrolidinium | SSZ-55; ZSM-12 |
| N-benzyl-N-cyclohexylpyrrolidinium | Beta |

TABLE A-continued

| Structure | Zeolite |
|---|---|
| 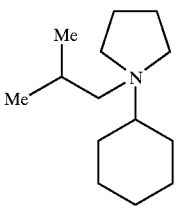 | SSZ-55 |
| 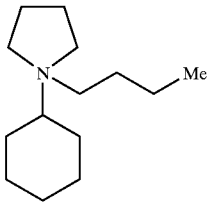 | SSZ-57 |
| 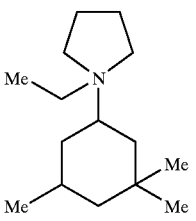 | SSZ-60 |
| 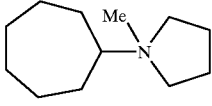 | ZSM-12 |
| 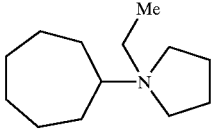 | ZSM-12 |
| 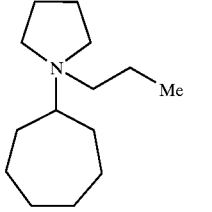 | SSZ-57 |
| 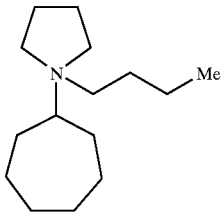 | ZSM-12 |
| 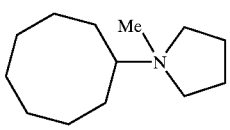 | ZSM-12 |
| 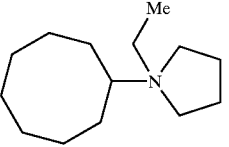 | ZSM-12 |
| 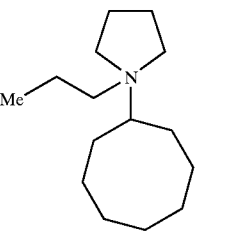 | SSZ-58 |
| 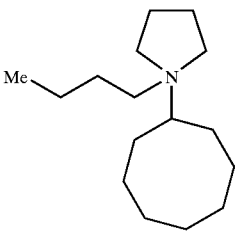 | SSZ-57; SSZ-58 |

Beta Zeolite

Beta zeolite is a well known zeolite. It is disclosed in Szostak, "Handbook of Molecular Sieves", Van Nostrand Reinhold, 1992 and in U.S. Pat. No. 3,308,069 (issued Mar. 7, 1967 to Wadlinger et al.), both of which are incorporated herein by reference in their entirety.

ZSM-11

ZSM-11 is also a well known zeolite. It is disclosed in Szostak, "Handbook of Molecular Sieves", Van Nostrand Reinhold, 1992 and in U.S. Pat. No. 3,709,979 (issued Jan. 9, 1973 to Chu), both of which are incorporated herein by reference in their entirety.

ZSM-12

ZSM-12 is another well known zeolite. It is disclosed in Szostak, "Handbook of Molecular Sieves", Van Nostrand Reinhold, 1992 and in U.S. Pat. No. 3,832,449 (issued Aug. 27, 1974 to Rosinski et al.), both of which are incorporated herein by reference in their entirety.

SSZ-37

SSZ-37 is a known zeolite. It is disclosed in U.S. Pat. No. 5,254,514 (issued Oct. 19, 1993 to Nakagawa), which is incorporated herein by reference in its entirety.

SSZ-55

SSZ-55 is disclosed in copending U.S. patent application Ser. No. 09/520,640, filed Mar. 7, 2000 which is incorporated herein by reference in its entirety. SSZ-55 is a zeolite having a composition, as synthesized and in the anhydrous state, in terms of mole ratios as follows:

$YO_2/W_cO_d$ 20–150
$M_{2/n}/YO_2$ 0.01–0.03
$Q/YO_2$ 0.02–0.05 where Y, W, c, d, M and n are as defined above and Q is an SDA. SSZ-55 can be prepared from reaction mixtures shown in the table below.

SSZ-55 Reaction Mixtures

|  | Typical | Preferred |
|---|---|---|
| $YO_2/W_aO_b$ | 20–150 | 35–60 |
| $OH^-/YO_2$ | 0.1–0.50 | 0.2–0.3 |
| $Q/YO_2$ | 0.05–0.5 | 0.1–0.2 |
| $M_{2/n}/YO_2$ | 0.02–0.4 | 0.1–0.25 |
| $H_2O/YO_2$ | 25–80 | 30–45 | where Y, W, a, b, M and n are as defined above and Q is the SDA.

SSZ-55 zeolites, as-synthesized, have a crystalline structure whose X-ray powder diffraction pattern exhibit the characteristic lines shown in Table I and is thereby distinguished from other zeolites.

TABLE I

As-Synthesized SSZ-55

| 2 Theta [a] | D | Relative Intensity [b] |
|---|---|---|
| 7.94 | 11.13 | S |
| 15.98 | 5.54 | M |
| 16.60 | 5.33 | S |
| 19.24 | 4.61 | M |
| 20.97 | 4.23 | VS |
| 21.93 | 4.05 | M |
| 22.48 | 3.95 | VS |
| 23.68 | 3.75 | M |
| 27.54 | 3.24 | M |
| 35.08 | 2.56 | W |

[a] ±0.2.
[b] The X-ray patterns provided are based on a relative intensity scale in which the strongest line in the X-ray pattern is assigned a value of 100: W (weak) is less than 20; M (medium) is between 20 and 40; S (strong) is between 40 and 60; VS (very strong) is greater than 60.

After calcination, the SSZ-55 zeolites have a crystalline structure whose X-ray powder diffraction pattern include the characteristic lines shown in Table II:

TABLE II

Calcined SSZ-55

| 2 Theta [a] | D | Relative Intensity |
|---|---|---|
| 7.94 | 11.13 | S |
| 13.60 | 6.51 | W |
| 16.67 | 5.31 | M |
| 19.31 | 4.59 | WM |
| 20.92 | 4.24 | WM |
| 22.00 | 4.04 | W |
| 22.56 | 3.94 | WM |
| 27.46 | 3.24 | W |
| 28.73 | 3.10 | W |
| 32.32 | 2.77 | W |

[a] ±0.2.

SSZ-57

Zeolite SSZ-57 has a composition, as synthesized and in the anhydrous state, in terms of mole ratios as follows:

$YO_2/W_cO_d$ 20–∞

$M_{2/n}/YO_2$ 0.01–0.03

$Q/YO_2$ 0.02–0.05 wherein Y, W, c, d, M and n are as defined above and Q is the SDA. SSZ-57 is prepared from reaction mixtures having the composition shown in the table below.

SSZ-57 Reaction Mixtures

|  | Typical | Preferred |
|---|---|---|
| $YO_2/W_aO_b$ | 20–∞ | 35–90 |
| $OH^-/YO_2$ | 0.1–0.50 | 0.2–0.3 |
| $Q/YO_2$ | 0.05–0.5 | 0.1–0.2 |
| $M_{2/n}/YO_2$ | 0.02–0.4 | 0.1–0.25 |
| $H_2O/YO_2$ | 25–80 | 30–50 | where Y, W, a, b, M, and n are as defined above and Q is the SDA.

SSZ-57 zeolites, as-synthesized, have a crystalline structure whose X-ray powder diffraction pattern exhibit the characteristic lines shown in Table III below and is thereby distinguished from other known zeolites.

TABLE III

As-Synthesized SSZ-57

| Two Theta (deg.) [a] | d-spacing | Relative Intensity |
|---|---|---|
| 7.7+/−0.15 | 11.5 | S |
| 8.8 | 10.0 | M |
| 14.65 | 6.04 | W |
| 15.55 | 5.69 | W |
| 17.65 | 5.02 | W |
| 20.85 | 4.26 | W |
| 23.05 | 3.86 | VS |
| 24.35 | 3.65 | M |
| 26.6 | 3.35 | W |
| 30.2 | 3.35 | W |
| 45.1 | 2.10 | W |

[a] ±0.2.

The complete X-ray diffraction pattern of a boron SSZ-57 zeolite is shown in Table IV below:

TABLE IV

Data for the As-Synthesized SSZ-57

| 2 Theta (deg.) [a] | d-spacing (Å) | Intensity I/Io × 100 |
|---|---|---|
| 7.74 | 11.413 | 32 |
| 8.78 | 10.063 | 22 |
| 11.72 | 7.545 | 7 |
| 12.42 | 7.121 | 5 |
| 13.86 | 6.384 | 2 |
| 14.26 | 6.206 | 3 |
| 14.66 | 6.038 | 4 |
| 15.56 | 5.690 | 4 |
| 17.14 | 5.169 | 3 |
| 17.64 | 5.024 | 3 |
| 18.96 | 4.677 | 3 |
| 19.28 | 4.600 | 1 |
| 20.86 | 4.255 | 4 |
| 21.82 | 4.070 | 1 |
| 23.04 | 3.857 | 100 |
| 23.44 | SH 3.792 | 5 |
| 24.32 | 3.657 | 12 |
| 25.98 | 3.427 | 3 |
| 26.62 | 3.346 | 5 |
| 27.75 | 3.212 | 1 |
| 28.96 | 3.081 | 3 |
| 29.46 | 3.030 | 2 |
| 30.22 | 2.955 | 6 |
| 31.54 | 2.834 | 1 |
| 32.36 | 2.764 | 1 |

TABLE IV-continued

Data for the As-Synthesized SSZ-57

| 2 Theta (deg.)[a] | d-spacing (Å) | Intensity I/Io × 100 |
|---|---|---|
| 34.10 | 2.627 | 2 |
| 35.40 | 2.534 | 2 |
| 35.76 | 2.509 | 2 |
| 36.18 | 2.481 | 2 |
| 36.90 | 2.434 | 1 |
| 37.64 | 2.388 | 1 |
| 43.24 | 2.091 | 1 |
| 45.12 | 2.008 | 7 |
| 45.30 | SH 2.000 | 4 |
| 47.52 | 1.912 | 1 |
| 48.52 | 1.875 | 2 |

SH = Shoulder
[a]±0.15

After calcination, the SSZ-57 zeolites have a crystalline structure whose X-ray powder diffraction pattern include the characteristic lines shown in Table V below.

TABLE V

Calcined SSZ-57

| Two Theta (deg.)[a] | d-spacing (Å) | Relative Intensity |
|---|---|---|
| 7.7 | 11.5 | VS |
| 8.8 | 10.0 | VS |
| 14.7 | 6.02 | M |
| 15.55 | 5.69 | W |
| 17.65 | 5.02 | W |
| 20.8 | 4.27 | W |
| 23.10 | 3.85 | VS |
| 24.4 | 3.65 | M |
| 26.65 | 3.34 | W |
| 30.25 | 2.95 | W |
| 45.25 | 2.00 | W |

[a]±0.15

The complete X-ray diffraction pattern for an SSZ-57 calcined zeolite is shown in Table VI below.

TABLE VI

Calcined SSZ-57

| 2 Theta (deg.)[a] | d-spacing (Å) | Intensity I/Io × 100 |
|---|---|---|
| 7.72 | 11.443 | 100 |
| 8.78 | 10.063 | 74 |
| 11.74 | 7.532 | 2 |
| 12.43 | 7.115 | 2 |
| 13.84 | 6.393 | 3 |
| 14.24 | 6.215 | 1 |
| 14.70 | 6.021 | 17 |
| 15.56 | 5.690 | 8 |
| 17.16 | 5.163 | 1 |
| 17.66 | 5.018 | 11 |
| 19.00 | 4.667 | 2 |
| 19.32 | 4.591 | 1 |
| 19.74 | 4.494 | 2 |
| 20.82 | 4.263 | 3 |
| 23.08 | 3.850 | 91 |
| 23.48 | SH 3.786 | 5 |
| 24.36 | 3.651 | 11 |
| 25.05 | 3.552 | 1 |
| 26.04 | 3.419 | 4 |
| 26.66 | 3.341 | 6 |
| 29.00 | 3.076 | 3 |
| 29.52 | 3.023 | 2 |
| 30.26 | 2.951 | 7 |
| 31.56 | 2.833 | 1 |
| 31.90 | 2.803 | 1 |

TABLE VI-continued

Calcined SSZ-57

| 2 Theta (deg.)[a] | d-spacing (Å) | Intensity I/Io × 100 |
|---|---|---|
| 34.20 | 2.620 | 2 |
| 35.46 | 2.529 | 1 |
| 35.84 | 2.503 | 2 |
| 36.28 | 2.474 | 1 |
| 36.96 | 2.430 | 1 |
| 37.76 | 2.380 | 1 |
| 43.97 | 2.058 | 1 |
| 45.26 | 2.002 | 16 |
| 46.22 | 1.962 | 1 |
| 47.58 | 1.910 | 1 |
| 48.60 | 1.872 | 1 |

SH = Shoulder
[a]±0.15

SSZ-58

SSZ-58 zeolites have a composition, as synthesized and in the anhydrous state, in terms of mole ratios as follows:

$YO_2/W_cO_d$ 20–∞

$M_{2/n}/YO_2$ 0.01–0.03

$Q/YO_2$ 0.02–0.05 wherein Y, W, c, d, M and n are as defined above and Q is the SDA. SSZ-58 is prepared from a reaction mixtures having the composition shown in the table below.

SSZ-58 Reaction Mixtures

| | Typical | Preferred |
|---|---|---|
| $YO_2/W_aO_b$ | >20 | 35–65 |
| $OH^-/YO_2$ | 0.10–0.50 | 0.15–0.25 |
| $Q/YO_2$ | 0.05–0.50 | 0.10–0.20 |
| $M_{2/n}/YO_2$ | 0.02–0.40 | 0.10–0.30 |
| $H_2O/YO_2$ | 25–100 | 30–50 | where Y, W, a, b, M and n are as defined above and Q is the SDA.

SSZ-58 zeolites, as-synthesized, have a crystalline structure whose X-ray powder diffraction pattern exhibit the characteristic lines shown in Table VII below.

TABLE VII

As-Synthesized SSZ-58

| 2 Theta (deg.)[a] | D | Relative Intensity |
|---|---|---|
| 7.1 | 12.4 | S |
| 7.7 | 11.5 | M |
| 9.9 | 8.93 | M |
| 10.5 | 8.42 | W |
| 12.1 | 7.31 | M |
| 17.3 | 5.12 | W |
| 19.7 | 4.50 | M |
| 21.0 | 4.23 | S |
| 21.9 | 4.06 | M |
| 22.35 | 3.97 | VS |

[a]±0.15

Table VIII below shows the X-ray powder diffraction lines for as-synthesized SSZ-58 including actual relative intensities.

TABLE VIII

As-Synthesized SSZ-58

| 2 Theta (deg.)[a] | d | $I/I_0 \times 100$ |
|---|---|---|
| 6.90 | 12.80 (Sh) | 6 |
| 7.06 | 12.51 | 39 |
| 7.72 | 1.44 | 16 |
| 9.86 | 8.963 (Sh) | 10 |
| 9.96 | 8.874 | 13 |
| 10.46 | 8.450 | 10 |
| 12.10 | 7.309 | 18 |
| 14.06 | 6.294 | 9 |
| 14.21 | 6.228 (Sh) | 7 |
| 15.46 | 5.727 | 5 |
| 15.68 | 5.647 | 6 |
| 16.12 | 5.494 | 4 |
| 17.24 | 5.139 | 14 |
| 17.36 | 5.104 (Sh) | 7 |
| 18.76 | 4.726 | 15 |
| 18.92 | 4.687 | 16 |
| 19.72 | 4.498 | 30 |
| 20.22 | 4.388 | 14 |
| 20.70 | 4.288 | 16 |
| 21.00 | 4.227 | 63 |
| 21.16 | 4.195 | 14 |
| 21.26 | 4.176 (Sh) | 12 |
| 21.88 | 4.059 | 26 |
| 22.28 | 3.987 (Sh) | 61 |
| 22.24 | 3.962 | 100 |
| 22.66 | 3.921 | 26 |
| 23.02 | 3.860 | 9 |
| 23.28 | 3.818 | 5 |
| 23.50 | 3.783 | 17 |
| 23.68 | 3.754 | 13 |
| 24.34 | 3.654 | 5 |
| 25.12 | 3.542 | 11 |
| 25.54 | 3.485 | 7 |
| 25.72 | 3.461 (Sh) | 4 |
| 26.12 | 3.409 | 8 |
| 26.58 | 3.351 | 7 |
| 27.30 | 3.264 | 11 |
| 27.58 | 3.232 | 7 |
| 27.94 | 3.191 | 5 |
| 28.50 | 3.129 (Sh) | 8 |
| 28.62 | 3.117 | 11 |
| 29.18 | 3.058 | 2 |
| 29.86 | 2.990 | 5 |
| 30.08 | 2.968 | 5 |
| 30.88 | 2.894 | 3 |
| 31.46 | 2.842 | 2 |
| 31.74 | 2.817 | 4 |
| 32.48 | 2.755 | 1 |
| 32.59 | 2.746 | 2 |
| 32.76 | 2.732 | 3 |
| 33.14 | 2.701 | 4 |
| 33.56 | 2.668 | 3 |
| 33.80 | 2.650 | 2 |
| 34.82 | 2.574 | 2 |
| 35.12 | 2.553 | 1 |
| 35.38 | 2.535 | 3 |
| 35.82 | 2.505 | 6 |
| 36.50 | 2.460 | 6 |
| 37.74 | 2.382 | 4 |
| 37.94 | 2.370 (Sh) | 2 |
| 38.44 | 2.340 | 2 |
| 39.29 | 2.291 | 2 |
| 39.62 | 2.273 | 1 |
| 41.10 | 2.194 | 1 |
| 43.12 | 2.096 | 2 |
| 43.30 | 2.086 | 5 |
| 43.50 | 2.079 | 2 |

[a]±0.15

After calcination, the SSZ-58 zeolites have a crystalline structure whose X-ray powder diffraction pattern include the characteristic lines shown in Table IX below.

TABLE IX

Calcined SSZ-58

| 2 Theta (deg.)[a] | d | Relative Intensity |
|---|---|---|
| 7.1 | 12.4 | VS |
| 7.7 | 11.5 | M |
| 9.9 | 8.93 | M |
| 10.5 | 8.42 | M |
| 12.1 | 7.31 | W |
| 17.3 | 5.12 | W |
| 19.8 | 4.48 | M |
| 21.0 | 4.23 | S |
| 21.9 | 4.06 | M |
| 22.4 | 3.97 | S |

[a]0.15

Table X below shows the X-ray powder diffraction lines for calcined SSZ-58 including actual relative intensities.

TABLE X

Calcined SSZ-58

| Two Theta (deg.)[a] | D | $I/I_o \times 100$ |
|---|---|---|
| 6.88 | 12.84 (Sh) | 17 |
| 7.06 | 12.51 | 100 |
| 7.70 | 11.47 | 22 |
| 9.86 | 8.963 (Sh) | 20 |
| 9.98 | 8.856 | 35 |
| 10.48 | 8.435 | 15 |
| 12.12 | 7.297 | 9 |
| 14.20 | 6.232 | 11 |
| 15.48 | 5.720 | 6 |
| 15.70 | 5.640 | 10 |
| 15.84 | 5.590 | 7 |
| 16.14 | 5.487 | 6 |
| 17.24 | 5.139 | 11 |
| 17.37 | 5.101 | 4 |
| 18.78 | 4.721 | 7 |
| 18.96 | 4.677 | 14 |
| 19.76 | 4.489 | 23 |
| 20.26 | 4.380 | 8 |
| 20.70 | 4.287 | 13 |
| 21.02 | 4.223 | 40 |
| 21.22 | 4.184 (Sh) | 9 |
| 21.90 | 4.055 | 18 |
| 22.35 | 3.975 (Sh) | 39 |
| 22.46 | 3.955 | 64 |
| 22.70 | 3.914 | 18 |
| 23.04 | 3.857 | 3 |
| 23.28 | 3.818 | 3 |
| 23.54 | 3.776 | 13 |
| 23.74 | 3.745 | 8 |
| 24.38 | 3.648 | 3 |
| 25.16 | 3.537 | 8 |
| 25.60 | 3.477 | 5 |
| 25.78 | 3.453 (Sh) | 4 |
| 26.14 | 3.406 | 5 |
| 26.64 | 3.343 | 6 |
| 27.34 | 3.259 | 6 |
| 27.64 | 3.225 | 6 |
| 27.98 | 3.186 | 4 |
| 28.58 | 3.121 (Sh) | 7 |
| 28.68 | 3.110 | 8 |
| 29.20 | 3.056 | 1 |
| 29.88 | 2.988 | 4 |
| 30.19 | 2.958 | 3 |
| 30.92 | 2.890 | 2 |
| 31.48 | 2.840 | 2 |
| 31.74 | 2.817 | 3 |
| 32.54 | 2.750 | 1 |
| 32.76 | 2.731 | 1 |

TABLE X-continued

Calcined SSZ-58

| Two Theta (deg.)[a] | D | I/Io × 100 |
|---|---|---|
| 33.18 | 2.698 | 2 |
| 33.62 | 2.664 | 2 |
| 33.86 | 2.645 | 2 |
| 34.88 | 2.570 | 1 |
| 35.20 | 2.548 | 1 |
| 35.42 | 2.532 | 2 |
| 35.90 | 2.499 | 5 |
| 36.54 | 2.457 | 4 |
| 37.80 | 2.378 | 3 |
| 38.00 | 2.366 (Sh) | 2 |
| 38.50 | 2.336 | 1 |
| 39.30 | 2.291 | 1 |
| 43.20 | 2.092 | 2 |
| 43.42 | 2.082 | 4 |
| 43.53 | 2.077 | 3 |

SSZ-60

SSZ-60 zeolites have a composition, as synthesized and in the anhydrous state, in terms of mole ratios as follows:

$YO_2/W_cO_d$ 20–180

$M_{2/n}/YO_2$ 0.01–0.03

$Q/YO_2$ 0.02–0.05 wherein Y, W, c, d, M and n are as defined above and Q is the SDA. SSZ-60 zeolites are prepared from reaction mixtures having the composition shown in the table below.

SSZ-60 Reaction Mixtures

| | Typical | Preferred |
|---|---|---|
| $YO_2/W_aO_b$ | >20 | 30–70 |
| $OH^-/YO_2$ | 0.10–0.50 | 0.20–0.30 |
| $Q/YO_2$ | 0.05–0.50 | 0.10–0.20 |
| $M_{2/n}/YO_2$ | 0.02–0.40 | 0.10–0.25 |
| $H_2O/YO_2$ | 30–80 | 35–45 | where Y, W, a, b, M and n are as defined above and Q is the SDA.

SSZ-60 zeolites, as-synthesized, have a crystalline structure whose X-ray powder diffraction pattern exhibit the characteristic lines shown in Table XI below.

TABLE XI

As-Synthesized SSZ-60

| Two Theta (deg.)[a] | d-spacing (Å) | Relative Intensity |
|---|---|---|
| 6.4 | 13.8 | M |
| 7.6 | 11.6 | M |
| 8.0 | 11.0 | S |
| 10.3 | 8.56 | M |
| 15.2 | 5.82 | W |
| 17.4 | 5.09 | M |
| 19.3 | 4.60 | M |
| 20.5 | 4.33 | S |
| 22.4 | 3.97 | VS |
| 24.2 | 3.69 | M |
| 27.2 | 3.28 | M |
| 28.1 | 3.17 | W |
| 35.9 | 2.50 | M |

[a]±0.2

Table XII below shows the X-ray powder diffraction lines for as-synthesized SSZ-60 including actual relative intensities.

TABLE XII

| Two Theta[a] | d-spacing (Å) | Intensity I/Io × 100 |
|---|---|---|
| 6.39 | 13.83 | 38 |
| 7.64 | Sh 11.56 | 24 |
| 7.98 | 11.07 | 49 |
| 10.29 | 8.588 | 19 |
| 13.40 | 6.604 | 6 |
| 15.19 | 5.828 | 12 |
| 17.44 | 5.080 | 36 |
| 19.30 | 4.596 | 36 |
| 20.53 | 4.322 | 57 |
| 21.49 | 4.132 | 13 |
| 22.36 | 3.973 | 100 |
| 23.39 | 3.801 | 16 |
| 24.12 | Sh 3.687 | 18 |
| 24.23 | 3.670 | 25 |
| 25.22 | 3.528 | 13 |
| 25.95 | 3.431 | 15 |
| 26.78 | Sh 3.327 | 12 |
| 27.16 | 3.281 | 27 |
| 28.08 | 3.176 | 19 |
| 29.05 | 3.071 | 6 |
| 30.72 | 2.908 | 6 |
| 31.34 | 2.852 | 5 |
| 32.65 | 2.740 | 6 |
| 33.63 | 2.663 | 5 |
| 35.87 | 2.594 | 31 |
| 37.47 | 2.502 | 4 |
| 39.58 | 2.398 | 4 |

[a]±0.2

After calcination, the SSZ-60 zeolites have a crystalline structure whose X-ray powder diffraction pattern include the characteristic lines shown in Table XIII below.

TABLE XIII

Calcined SSZ-60

| Two Theta (deg.)[a] | d-spacing (Å) | Relative Intensity |
|---|---|---|
| 6.4 | 13.8 | VS |
| 7.6 | 11.6 | S |
| 8.0 | 11.0 | VS |
| 10.25 | 8.62 | S |
| 15.1 | 5.86 | W |
| 17.5 | 5.06 | W |
| 19.2 | 4.62 | M |
| 20.4 | 4.35 | M |
| 22.3 | 3.98 | S |
| 24.2 | 3.67 | W |
| 27.1 | 3.29 | W |
| 28.0 | 3.18 | W |
| 35.7 | 2.51 | W |

[a]±0.2

Table XIV below shows the X-ray powder diffraction lines for calcined SSZ-60 including actual relative intensities.

TABLE XIV

| Two Theta[a] | d-spacing (Å) | Intensity I/Io × 100 |
|---|---|---|
| 6.36 | 13.88 | 100 |
| 7.63 | Sh 11.58 | 44 |
| 7.98 | 11.07 | 76 |
| 10.25 | 8.625 | 48 |
| 15.11 | 5.860 | 5 |
| 16.12 | 5.495 | 4 |
| 17.47 | 5.073 | 10 |

TABLE XIV-continued

| Two Theta(a) | d-spacing (Å) | Intensity I/Io × 100 |
|---|---|---|
| 18.07 | 4.904 | 2 |
| 19.20 | 4.620 | 40 |
| 19.70 | 4.503 | 2 |
| 20.44 | 4.342 | 39 |
| 22.28 | 3.987 | 64 |
| 23.32 | 3.811 | 15 |
| 24.19 | 3.676 | 14 |
| 25.17 | 3.536 | 9 |
| 25.86 | 3.442 | 12 |
| 26.59 | 3.349 | 10 |
| 27.11 | 3.286 | 13 |
| 28.00 | 3.185 | 6 |
| 29.03 | 3.074 | 4 |
| 30.56 | 2.923 | 3 |
| 31.32 | 2.854 | 5 |
| 32.57 | 2.747 | 4 |
| 33.53 | 2.671 | 4 |
| 35.70 | 2.513 | 18 |

(a)±0.2

Calcination can result in changes in the intensities of the peaks as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

The zeolites prepared by the present process are useful in hydrocarbon conversion reactions. Hydrocarbon conversion reactions are chemical and catalytic processes in which carbon-containing compounds are changed to different carbon-containing compounds. Examples of hydrocarbon conversion reactions include catalytic cracking, hydrocracking, dewaxing, alkylation, isomerization, olefin and aromatics formation reactions, and aromatics isomerization.

The following examples demonstrate, but do not limit, the present invention.

EXAMPLES

There are numerous variations on the embodiments of the present invention illustrated in the Examples which are possible in light of the teachings supporting the present invention. It is therefore understood that within the scope of the following claims, the invention may be practiced otherwise than as specifically described or exemplified.

Example A

Synthesis of SDA N-butyl-N-cyclohexylpyrrolidiniumcation

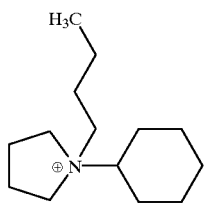

I. Synthesis of N-cyclohexylpyrrolidine

The structure-directing agent (SDA) is synthesized using the reaction sequence described in the scheme below. A three neck 3000-ml flask is charged with 100 gm (1.4 mole) of pyrrolidine, 50 gm of cyclohexanone (0.51 mole) and 1000 ml anhydrous hexane. To the resulting solution, 122 gm (1.022 mole) of anhydrous magnesium sulfate is added and the mixture is mechanically stirred and heated at reflux (the reaction is monitored by NMR analysis) for 96 hrs. The reaction mixture is filtered through a fritted glass funnel. The filtrate is concentrated under reduced pressure on a rotary evaporator to give 75 gm of a clear (yellow-tinted) oily substance. $^1$H-NMR and $^{13}$C-NMR spectra are acceptable for the desired product 1-(1-pyrrolidino)cyclohexene. Saturation of 1-(1-pyrrolidino)cyclohexene, to give N-cyclohexylpyrrolidine, is accomplished in quantitative yield by hydrogenation in ethanol at a 55 psi pressure of hydrogen gas in the presence of 10% Pd on activated carbon.

N-cyclohexylpyrrolidine is also obtained by lithium aluminum hydride reduction of 1-cyclohexyl-2-pyrrolidinone. To a suspension of 22.7 gm (0.6 mole) of lithium aluminum hydride in 600 ml anhydrous tetrahydrofuran (THF) in a three-neck 3000-ml reaction flask at 0° C. (ice bath), 50 gm (0.3 mole) of 1-cyclohexyl-2-pyrrolidinone in 100 ml THF are added drop wise via an addition funnel. Once the addition is complete, the ice-bath is replaced with a heating mantle and the reaction is refluxed and mechanically stirred overnight. The reaction is kept protected from moisture. The reaction mixture is then cooled down to 0° C. (the heating mantle is replaced with an ice-bath) and the reaction mixture is diluted with 500 ml ether. The reaction is worked up by adding 75 ml of 15 wt. % NaOH aqueous solution drop wise at 0° C. with vigorous stirring. Once the addition of NaOH is finished, 15 ml of $H_2O$ is added and the reaction mixture is left to stir for an additional 15 min. The grayish looking mixture turns into a two-phase mixture with a clear colorless liquid and a white precipitate. The mixture is filtered and the solids are thoroughly rinsed with ether. The filtrate and the ether rinses are combined and dried over anhydrous magnesium sulfate. Filtration and concentration of the filtrate under reduced pressure on a rotary evaporator give the desired reduction product as colorless oil in 95.7% yield (44 gm).

II. Quaternization (Synthesis of N-butyl-N-cyclohexylpyrrolidinium iodide)

To a solution of 50 gm (0.326 mole) of N-cyclohexylpyrrolidine in 600 ml anhydrous methanol, 120 gm (0.652 mole) of butyl iodide is added. The reaction is mechanically stirred for 48 hours at room temperature. Then, an additional equivalent of butyl iodide and one equivalent (33.7 gm; 0.326 mole) of potassium bicarbonate are added and the reaction is stirred at refluxing temperature for 72 hours. The reaction mixture is concentrated under reduced pressure on a rotary evaporator to give an off-white-colored solid material. The solids are rinsed several times with chloroform and filtered after each rinse. All the chloroform rinses are combined and concentrated to give a white powder whose NMR data is acceptable for the desired quaternary ammonium iodide salt. The reaction affords 95 gm (86% yield) of the product. The iodide salt is purified by recrystallization. This is done by completely dissolving the iodide salt in acetone and then precipitating by the addition of ethyl ether to the acetone solution. The procedure gives 87 gm of white powder with very clean $^1$H and $^{13}$C-NMR spectra for the product (N-butyl-N-cyclohexylpyrrolidinium iodide).

III. Ion Exchange (Synthesis of N-butyl-N-Cyclohexylpyrrolidinium Hydroxide)

N-butyl-N-cyclohexylpyrrolidinium iodide salt (85 gm; 0.25 mol) is dissolved in 300 ml water in a 500-ml volume plastic bottle. To the solution, 300 gm of Ion-Exchange Resin-OH (BIO RAD® AH1-X8) is added and the mixture is stirred at room temperature overnight. The mixture is filtered and the solids are rinsed with additional 85 ml of water. The original filtrate and the rinse are combined and a small amount is titrated with 0.1N HCl to indicate the presence of 0.24 mol hydroxide (0.24 mol N-butyl-N-cyclohexylpyrrolidinium hydroxide) in the solution. The synthetic procedure described above is depicted below.

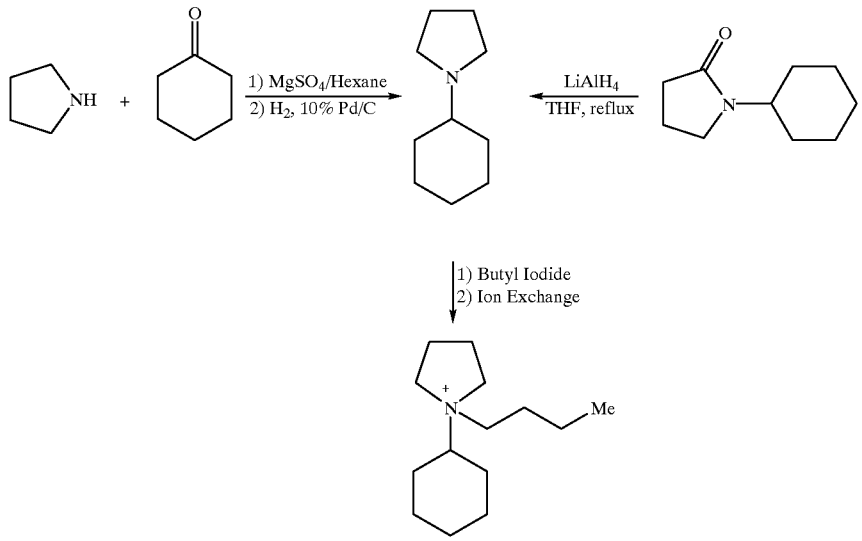

The pyrrolidinium cation SDA's shown in Table A above are prepared using a similar procedure and reaction scheme shown above.

Example B

Synthesis of N-ethyl-N-(3,3,5-trimethylcyclohexyl) pyrrolidinium cation
Synthesis of N-(3,3,5-trimethylyyclohexyl)pyrrolidine The structure-directing agent (SDA) is synthesized using the reaction sequence described in the scheme below.

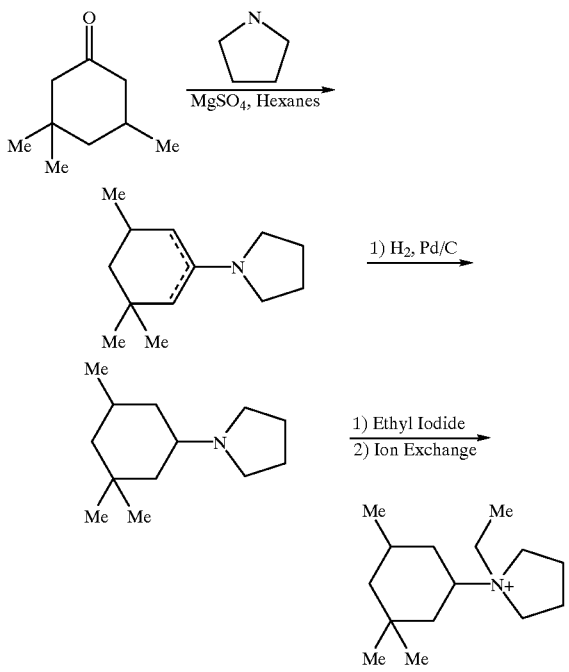

Synthesis of the Parent Amine N-(3,3,5-trimethylcyclohexyl)pyrrolidine

In a 3-liter three neck flask a 150 gm (2.13 mole) of pyrrolidine, 100 gm of 3,5,5-trimethylcyclohexanone (0.71 mole) are mixed in a 1500 ml anhydrous hexane. To the resulting solution, 150 gm (1.25 mole) of anhydrous magnesium sulfate is added and the mixture is mechanically stirred and heated at reflux (the reaction is monitored by NMR analysis) for 132 hours. The reaction mixture is filtered through a fritted glass funnel. The filtrate is concentrated under reduced pressure on a rotary evaporator to give 133 gm of an isomeric mixture of the desired enamine as indicated by $^1$H-NMR and $^{13}$C-NMR analysis [(3,3,5-trimethylcyclohex-enyl)pyrrolidine and (3,3,5-trimethylcyclohex-enyl)pyrrolidine]. Saturation of the enamine mixture, to give N-(3,5,5-trimethylcyclohexyl) pyrrolidine, is accomplished in quantitative yield by hydrogenation in ethanol at a 55 psi pressure of hydrogen gas in the presence of 10% Pd on activated carbon.

Quaternization of N-(3,3,5-trimethylcyclohexyl)pyrrolidine (Synthesis of N-ethyl-N-(3,3,5-trimethcyclohexyl) pyrrolidinium iodide)

To a solution of 131 gm (0.67 mole) of N-(3,3,5-trimethylcyclohexyl)pyrrolidine in 1000 ml anhydrous methanol, 210 gm (1.34 mole) of ethyl iodide is added. The reaction is mechanically stirred for 3 days at room temperature. Then, an additional equivalent of ethyl iodide and one equivalent (67.7 gm; 0.0.67 mole) of potassium bicarbonate are added and the reaction is stirred at refluxing temperature for 72 hours. The reaction mixture is concentrated under reduced pressure on a rotary evaporator to give an off-white-colored solid material. The solids are rinsed several times with chloroform and filtered after each rinse. All the chloroform rinses are combined and concentrated to give a white powder whose NMR data are acceptable for the desired quaternary ammonium iodide salt. The reaction affords 218 gm (93% yield) of the product. The iodide salt is purified by re-crystallization in acetone and ether. This is done by completely dissolving the iodide salt in acetone and, then, the precipitation of the product is facilitated by addition of ethyl ether to the acetone solution. Re-crystallization gives 211 gm of the product as white powder (pure by $^1$H and $^{13}$C-NMR NMR analysis).

Ion Exchange (Synthesis of N-ethyl-N-(3,3,5-trimethylcyclohexyl)pyrrolidinium hydroxide)

To a solution of N-ethyl-N-(3,3,5-trimethylcyclohexyl) pyrrolidinium iodide salt (100 gm; 0.285 mole) in 350 ml water in a 1-liter plastic bottle, 340 gm of Ion-Exchange Resin-OH (BIO RAD® AH1-X8) is added and the mixture is gently stirred at room temperature overnight. The mixture is filtered and the solids rinsed with additional 75 ml of water. Titration analysis with 0.1N HCl gives a total yield of 0.215 mole of hydroxide ions (0.215 mole N-ethyl-N-(3,3,5-trimethylcyclohexyl)pyrrolidinium hydroxide).

Example C

Synthesis of N-ethyl-N-(2,4,4-trimethylcyclopentyl) pyrrolidinium cation

N-ethyl-N-(2,4,4,-trimethylcyclopentyl)pyrrolidinium cation is synthesized using the synthetic scheme described above starting from pyrrolidine and 2,4,4-trimethylcyclopentanone.

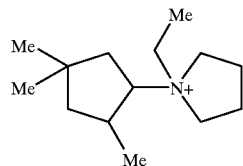

Example D

Synthesis of N-butyl-N-cyclooctylpyrrolidinium hydroxide

I. Synthesis of N-cyclooctylpyrrolidine

A three-neck 3000 ml. flask is charged with 75 gm. (1.05 moles) of pyrrolidine, 51 gm. cyclooctanone (0.4 mole) and 80 ml. anhydrous hexane. To the resulting solution, 80 gm. (0.8 mole) of anhydrous magnesium sulfate is added and the mixture is mechanically stirred and heated at reflux (the reaction was monitored by NMR analysis) for 108 hours. The reaction mixture is filtered through a fritted glass funnel. The filtrate is concentrated at reduced pressure on a rotary evaporator to give 70.5 gm. of a clear (yellow-tinted) oily substance. $^1$H-NMR and 13C-NMR spectra are acceptable for the desired product, 1-(1-pyrrolino)cyclooctene. Saturation of the 1-(1-pyrrolino)cyclooctene to give N-cyclooctylpyrrolidine is accomplished in 98% yield by catalytic hydrogenation in ethanol at a 55 psi pressure of hydrogen gas in the presence of 10% Pd on activated carbon.

II. Quaternization (Synthesis of N-butyl-N-cyclooctylpyrrolidinium iodide)

To a solution of 60 gms. (0.33 mole) of N-cyclooctyl pyrrolidine in 600 ml. anhydrous methanol, 150 gm. (0.825 mole) of butyl iodide is added. The reaction mixture is refluxed while stirring for four days. Then an additional equivalent of butyl iodide and one equivalent (33 gm., 0.33 mole) of potassium bicarbonate are added and the mixture is stirred at refluxing temperature for an additional 36 hours. The reaction mixture is concentrated at reduced pressure on a rotary evaporator to give an off-white colored solid material. The solids are rinsed several times with chloroform and filtered after each rinse. All the chloroform rinses are combined and concentrated to give a white powder whose NMR data are acceptable for the desired quaternary ammonium iodide salt. The reaction affords 109 gm. (90% yield) of N-butyl-N-cyclooctylpyrrolidinium iodide. The iodide salt is purified by recrystallization by completely dissolving the iodide salt in acetone, and then precipitating by the addition of ethyl ether to the acetone solution. This procedure gives 98 gms. of white powder with very clean $^1$H and $^{13}$C-NRM spectra.

III. Ion Exchange (Synthesis of N-butyl-N-cyclooctylpyrrolidinium hydroxide)

N-butyl-N-cyclooctylpyrrolidinium iodide salt (95 gms., 0.26 mole) is dissolved in 300 ml. water in a 1000 ml. plastic bottle. To the solution, 300 gms. of Ion Exchange Resin OH (BIO RAD® AG1-X8) is added and the mixture is stirred at room temperature overnight. The mixture is filtered and the solids rinsed with an additional 250 ml. of water. The original mixture is filtered and the rinses are combined and a small amount is titrated with 0.1N HCl to indicate the presence of 0.24 mol hydroxide (0.24 mol N-butyl-N-cyclooctylpyrrolidinium hydroxide) in the solution.

The synthetic procedure described above is depicted below.

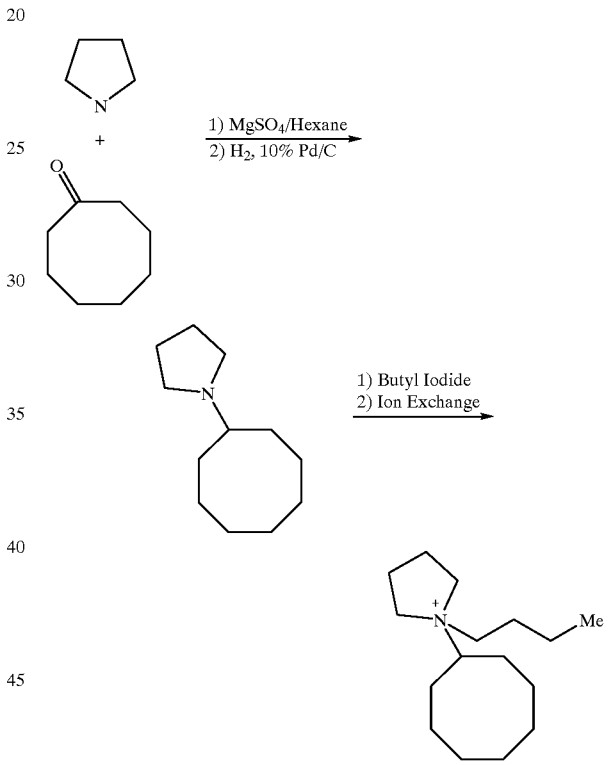

In a manner similar to that of Example D, N-cyclooctyl-N-propylpyrrolidinium cation is prepared.

Example 1

Synthesis of Boron-SSZ-57

A 23 cc Teflon liner is charged with 4.8 gm of 0.625M aqueous solution of N-butyl-N-cyclohexylpyrrolidinium hydroxide (3 mmol template), 1.2 gm of 1M aqueous solution of NaOH (1.2 mmol NaOH) and 6 gm of de-ionized water. To this mixture, 0.06 gm of sodium borate decahydrate (0.157 mmol of $Na_2B_4O_7 \cdot 10H_2O$; about 0.315 mmol $B_2O_3$) are added and stirred until completely dissolved. Then, 0.9 gm of CABOSIL® M-5 amorphous fumed silica, (about 14.7 mmol $SiO_2$) is added to the solution and the mixture was thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM) at six day intervals. The reaction is completed after heating for 18 days at the conditions described above. Once the crystallization is complete, the starting reaction gel turns to a mixture comprising of a clear liquid layer with solids (powder) that settles to the bottom. The mixture is filtered through a fritted-glass funnel. The collected solids are thoroughly washed with water and then rinsed with acetone (10 ml) to remove any organic residues. The solids are allowed to air-dry over night and then dried in an oven at 120° C. for 1 hour. The reaction affords 0.8 gram of a very fine powder. SEM shows the presence of only one crystalline phase. The X-ray analysis of the powder indicates that the material is SSZ-57.

SSZ-57 is prepared in a similar manner using in turn a N-methyl-N-cycloheptyl pyrrolidium cation and a N-butyl-N-cyclooctyl pyrrolidinium cation as the SDA.

Example 2

Synthesis of SSZ-57

Table 1 below shows the results of making B-SSZ-57 at varying SiO2/B2O3 ratios. The synthesis is carried out as described in Example 1 keeping the amounts of all reagents constant but varying the amount of sodium borate decahydrate.

TABLE 1

Synthesis of SSZ-57 at varying $SiO_2/B_2O_3$ ratios

| $SiO_2/B_2O_3$ | $SiO_2$/Na | Days | Observed Products |
|---|---|---|---|
| ∞ (all Silica) | 12.25 | 15 | SSZ-57 |
| 280 | 11.74 | 15 | SSZ-57 |
| 140 | 11.26 | 15 | SSZ-57 |
| 93.6 | 10.83 | 18 | SSZ-57 |
| 70 | 10.42 | 18 | SSZ-57 |
| 56 | 10.05 | 18 | SSZ-57 |
| 46.3 | 9.7 | 18 | SSZ-57 |
| 40 | 9.38 | 18 | SSZ-57 |
| 35 | 9.07 | 18 | SSZ-57 |
| 31 | 8.8 | 18 | SSZ-57 |
| 28 | 8.52 | 18 | SSZ-57 |
| 25.5 | 8.27 | 18 | SSZ-57 |
| 23.3 | 8.03 | 18 | SSZ-57 |
| 21.55 | 7.81 | 21 | SSZ-57 & trace of Layered |
| 18.67 | 7.4 | 21 | SSZ-57 & trace of layered Material |

The synthesis is carried out exactly as described in Example 1 keeping the amount of NaOH, water and CABOSIL-M-5 the same while varying the amount of $Na_2B_4O_7 \cdot 10H_2O$. $SiO_2/OH=3.5$, $H_2O/SiO_2=45$. The reactions are carried out at 160° C. and 43 rpm.

Example 3

Seeded Synthesis of Boron-SSZ-57

A 23 cc Teflon liner is charged with 4.8 gm of 0.625M aqueous solution of N-butyl-N-cyclohexylpyrrolidinium hydroxide (3 mmol template), 1.2 gm of 1M aqueous solution of NaOH (1.2 mmol NaOH) and 6 gm of de-ionized water. To this mixture, 0.06 gm of sodium borate decahydrate (0.157 mmol of $Na_2B_4O_7 \cdot 10H_2O$; ~0.315 mmol $B_2O_3$) is added and stirred until completely dissolved. Then, 0.9 gm of CABOSIL® M-5 amorphous fumed silica (~14.7 mmol $SiO_2$) and 0.04 gm of SSZ-57 (the product of Example 1) are added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM) at two day intervals. The reaction is completed after heating for 6 days at the conditions described above. Once the crystallization is complete, the starting reaction gel turns to a mixture comprising a clear liquid layer with solids (powder) that settle to the bottom. The mixture is filtered through a fritted-glass funnel. The collected solids are thoroughly washed with water and then rinsed with acetone (10 ml) to remove any organic residues. The solids are allowed to air-dry over night and then dried in an oven at 120° C. for one hour. The reaction affords 0.86 gram of a very fine powder. SEM shows the presence of only one crystalline phase. Powder X-ray diffraction pattern of the product indicates the material is SSZ-57.

Example 4

Synthesis of Aluminum-SSZ-57 (Using LZ-Y52 as Aluminum Source)

A 23 cc Teflon liner is charged with 3.6 gm of 0.625M aqueous solution of N-butyl-N-cyclohexylpyrrolidinium hydroxide (2.25 mmol template), 1.5 gm of 1M NaOH aqueous solution (1.5 mmol NaOH) and 2.3 gm of de-ionized water. To this solution, 0.26 gm of sodium-Y zeolite (Union Carbide LZ-Y52: $SiO_2/Al_2O_3=5$) and 0.80 gm of CABOSIL® M-5 amorphous fumed silica, (about 13 mmol $SiO_2$) are added, consecutively. The mixture is thoroughly stirred and the resulting gel is capped off and placed in a Parr bomb Steel reactor and heated in an oven at 160° C. while rotating at 43 rpm. The reaction is monitored by checking the gel's pH, and by looking for crystal formation using Scanning Electron Microscopy (SEM) at six day intervals. The reaction is completed after heating at the conditions described above for 6 days. The completed reaction mixture appears as a colorless liquid with fine white solid settled at the bottom of the Teflon liner. The mixture is filtered through a fritted-glass funnel, and the obtained white solids are washed generously with water and then rinsed with a small a mount of acetone and allowed to air-dry overnight. The obtained solids are further dried in an oven at 120° C. for one hour. The reaction yields 0.82 gm of SSZ-57 as indicated by the powder X-ray analysis of the product and a trace of the starting reagent LZ-Y52 zeolite.

Example 5

Synthesis of Al-SSZ-57

Table 2 below shows the results of attempts at making Al-SSZ-57 at varying $SiO_2/Al_2O_3$ ratios. The synthesis is carried out exactly as described in Example 4 but varying the amount of LZ-Y52 while keeping all the amounts of all other reagents constant.

TABLE 2

Synthesis of SSZ-57 at varying $SiO_2/Al_2O_3$ ratios

| $SiO_2/Al_2O_3$ | $SiO_2$/Na | Days | Observed Products |
|---|---|---|---|
| ∞ (all Silica) | 8.7 | 18 | SSZ-57, trace of Layered |
| 317 | 8.4 | 12 | SSZ-57 |
| 158.5 | 8.1 | 12 | SSZ-57 |
| 107.5 | 7.78 | 12 | SSZ-57 |
| 82.5 | 7.5 | 12 | SSZ-57 |
| 66.9 | 7.3 | 12 | SSZ-57 |

TABLE 2-continued

Synthesis of SSZ-57 at varying $SiO_2/Al_2O_3$ ratios

| $SiO_2/Al_2O_3$ | $SiO_2/Na$ | Days | Observed Products |
|---|---|---|---|
| 56.5 | 7.1 | 12 | SSZ-57 |
| 49 | 6.9 | 12 | SSZ-57, trace LZ-Y52 |
| 43.5 | 6.7 | 12 | SSZ-57, trace LZ-Y52 |
| 39 | 6.6 | 12 | SSZ-57, trace LZ-Y52 |
| 35.8 | 6.4 | 12 | SSZ-57 (major), LZ-Y52 (minor) |
| 33 | 6.26 | 12 | SSZ-57 (major), LZ-Y52 (minor) |
| 30.8 | 6.16 | 12 | SSZ-57 (major), LZ-Y52 (minor) |
| 26.3 | 5.85 | 18 | SSZ-57 (major), LZ-Y52 (minor) |
| 23.8 | 5.66 | 18 | SSZ-57 (major), LZ-Y52 (minor) |
| 20 | 5.32 | 18 | SSZ-57 (major), LZ-Y52 (minor |

The reactions are carried out exactly as in Example 4 above (160° C. and 43 rpm) using Union Carbide's LZ-Y52 as the aluminum source and CABOSIL-M-5 as the $SiO_2$ source. $SiO_2/OH=8.7$, $H_2O/SiO_2=28$.

SSZ-57 is prepared in a similar manner using N-propyl-N-cycloheptylpyrrolidinium cation or N-butyl-N-cyclooctylpyrrolidinium as the templating agent.

Example 6

Synthesis of Al-SSZ-57 (Using Reheis F-2000 as Aluminum Source)

A 23 cc Teflon liner is charged with 3.6 gm of 0.625M aqueous solution of N-butyl-N-cyclohexylpyrrolidinium hydroxide (2.25 mmol template), 1.5 gm of 1M NaOH aqueous solution (1.5 mmol NaOH) and 6.8 gm of de-ionized water. To this solution, 0.032 gm of Reheis F-2000 alumina (53 wt. % $Al_2O_3$) are added and stirred until completely dissolved. Then, 0.90 gm of CABOSIL® M-5 amorphous fumed silica, (about 14.7 mmol $SiO_2$) is added to the mixture and the resulting gel is capped off and placed in a Parr bomb Steel reactor and heated in an oven at 170° C. while rotating at 43 rpm. The reaction is monitored by checking the gel's pH, and by looking for crystallization using Scanning Electron Microscopy (SEM) at six day intervals. The reaction is completed after heating at the conditions described above for 18 days. The completed reaction mixture appears as a colorless liquid with fine white solid settled at the bottom of the Teflon liner. The mixture is filtered through a fritted-glass funnel, and the obtained white solids are washed generously with water and then rinsed with a small a mount of acetone and allowed to air-dry overnight. Then, the solids are further dried in an oven at 120° C. for one hour. The reaction yields 0.85 gm of SSZ-57 as indicated by the powder X-ray analysis of the product.

Example 7

Seeded Synthesis of Al-SSZ-57 (Using Reheis F-2000 as Aluminum Source)

A 23 cc Teflon liner is charged with 3.6 gm of 0.625M aqueous solution of N-butyl-N-cyclohexylpyrrolidinium hydroxide (2.25 mmol template), 1.5 gm of 1M NaOH aqueous solution (1.5 mmol NaOH) and 6.8 gm of de-ionized water. To this solution, 0.032 gm of Reheis F-2000 (53 wt. % $Al_2O_3$) is added and stirred until completely dissolved. Then, 0.90 gm of CABOSIL-M-5 (~14.7 mmol $SiO_2$) and 0.04 gm of SSZ-57 are added to the mixture. The resulting gel is thoroughly stirred, capped off and placed in a Parr Steel reactor and heated in an oven at 170° C. while rotating at 43 rpm. The reaction is monitored by checking the gel's pH, and by looking for crystallization using Scanning Electron Microscopy (SEM). The reaction is completed after heating at the conditions described above for 5 days. The completed reaction mixture appears as a colorless liquid with fine white solid settled at the bottom of the Teflon liner. The mixture is filtered through a fritted-glass funnel, and the obtained white solids are washed generously with water and then rinsed with a small amount of acetone and allowed to air-dry overnight. Then, the solids are further dried in an oven at 120° C. for 1 hour. The reaction yields 0.9 gm of SSZ-57 as indicated by the powder X-ray analysis of the product.

Example 8

Synthesis of All Silica-SSZ-57

A 23 cc Teflon liner is charged with 4.8 gm of 0.625M aqueous solution of N-butyl-N-cyclohexylpyrrolidinium hydroxide (3 mmol template), 1.2 gm of 1M aqueous solution of NaOH (1.2 mmol NaOH) and 6 gm of de-ionized water. Then, 0.9 gm of CABOSIL® M-5 amorphous fumed silica, (about 14.7 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM) at six day intervals. The reaction is completed after heating for 18 days at the conditions described above. Once the crystallization is complete, the starting reaction gel turns to a mixture comprising of a clear liquid layer with solids (powder) that settled to the bottom. The mixture is filtered through a fritted-glass funnel. The collected solids are thoroughly washed with water and then rinsed with acetone (10 ml) to remove any organic residues. The solids are allowed to air-dry over night and then dried in an oven at 120° C. for one hour. The reaction affords 0.86 gram of a very fine powder. SEM shows the presence of only one crystalline phase. The X-ray analysis of the powder indicates that the material is SSZ-57.

Example 9

Preparation of Borosilicate SSZ-58

A 23 cc. Teflon liner is charged with 6.9 grns. of 0.435M aqueous solution of N-butyl-N-cyclooctylpyrrolidinium hydroxide (3 mmol), 1.2 gms. of 1M aqueous solution of NaOH (1.2 mmol NaOH) and 3.9 gms. of deionized water. To the resulting mixture, 0.06 gm. of sodium borate decahydrate (0.157 mmol of sodium borate decahydrate, about 0.315 mmol $B_2O_3$) is added and stirred until completely dissolved. Then 0.9 gm. of CABOSIL® M-5 amorphous fumed silica (about 14.7 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM) at six day intervals. The reaction is completed after heating for 12 days at the conditions described above. Once the crystallization is complete, the starting reaction gel turns to a mixture comprising a clear liquid layer with solids (powder) that settle to the bottom. The mixture is filtered through a fritted glass funnel. The collected solids are thoroughly washed with water and then rinsed with acetone (10 ml.) to remove any organic residues. The solids are allowed to air-dry overnight and then they are oven-dried at 120° C. for one hour. The reaction affords 0.78 gm. of a very fine powder. SEM shows the presence of only one crystalline phase. The X-ray analysis of the powder indicates that the material is SSZ-58.

SSZ-58 is prepared in a similar manner using a N-cyclooctyl-N-propylpyrrolidinium cation as the SDA.

Examples 10–23

Synthesis of Borosilicate SSZ-58

The synthesis of Example 2 is repeated keeping the amount of NaOH, water and CABOSIL® M-5 the same while varying the amount of $Na_2B_4O_7.10H_2O$. The $SiO_2/OH$ mole ratio is 3.5, the $H_2O/SiO_2$ mole ratio is 45 and the $SiO_2/B_2O_3$ and $SiO_2/Na$ mole ratios are as indicated in the table below. The reactions are carried out at 160° C. and 43 rpm.

| Example No. | $SiO_2/B_2O_3$ | $SiO_2/Na$ | Days | Products |
|---|---|---|---|---|
| 10 | 280 | 11.74 | 12 | SSZ-58 |
| 11 | 140 | 11.26 | 12 | SSZ-58 |
| 12 | 93.6 | 10.83 | 12 | SSZ-58 |
| 13 | 70 | 10.42 | 12 | SSZ-58 |
| 14 | 56 | 10.05 | 12 | SSZ-58 |
| 15 | 46.3 | 9.7 | 12 | SSZ-58 |
| 16 | 40 | 9.38 | 12 | SSZ-58 |
| 17 | 35 | 9.07 | 12 | SSZ-58 |
| 18 | 31 | 8.8 | 18 | SSZ-58 |
| 19 | 28 | 8.52 | 18 | SSZ-58 + layered mat'l |
| 20 | 25.5 | 8.27 | 18 | SSZ-58 + layered mat'l |
| 21 | 23.3 | 8.03 | 18 | SSZ-58 (major) + layered mat'l (minor) |
| 22 | 21.55 | 7.81 | 18 | SSZ-58 (major) + layered mat'l (minor) |
| 23 | 18.67 | 7.4 | 21 | SSZ-58 + layered mat'l (minor) |

Example 24

Synthesis of Aluminosilicate SSZ-58

A 23 cc. Teflon liner is charged with 5.2 gms. of 0.435M aqueous solution of N-butyl-N-cyclooctylpyrrolidinium hydroxide (2.25 mmol Template A), 1.5 gms. of 1M NaOH aqueous solution (1.5 mmol NaOH) and 0.75 gm. of deionized water. To the resulting solution, 0.25 gm. of sodium-Y zeolite (Union Carbide LZ-Y52: $SiO_2/Al_2O_3$=5) and 0.80 gm. of CABOSIL® M-5 amorphous fumed silica (about 13 mmol $SiO_2$) are added, consecutively. The resulting mixture is thoroughly stirred and the resulting gel is capped off and placed in a Parr bomb steel reactor and heated in an oven at 160° C. while rotating at 43 rpm. The reaction is monitored by checking the gel's pH, and by looking for crystal formation using SEM at six day intervals. The reaction is completed after heating at the conditions described above for six days. The completed reaction mixture appears as a colorless liquid with fine white solid settled to the bottom of the Teflon liner. The mixture is filtered through a fritted glass funnel, and the obtained white solids are washed generously with water and then rinsed with a small amount of acetone and allowed to air-dry overnight. The solids are further dried in an oven at 120° C. for one hour. The reaction yields 0.81 gm. of SSZ-58.

Examples 25–39

Synthesis of Aluminosilicate SSZ-58

The synthesis of Example 24 is repeated using LZ-Y52 as the aluminum source and CABOSIL® M-5 as the $SiO_2$ source. The $SiO_2/OH$ mole ratio is 8.7, the $H_2O/SiO_2$ mole ratio is 28 and the $SiO_2/Al_2O_3$ and $SiO_2/Na$ mole ratios are as indicated in the table below. The reactions are carried out at 160° C. and 43 rpm.

| Example No. | $SiO_2/Al_2O_3$ | $SiO_2/Na$ | Products |
|---|---|---|---|
| 25 | 317 | 8.4 | SSZ-58 + Trace LZ-Y52 |
| 26 | 158.5 | 8.1 | SSZ-58 + Trace LZ-Y52 |
| 27 | 107.5 | 7.78 | SSZ-58 + Trace LZ-Y52 |
| 28 | 82.5 | 7.5 | SSZ-58 |
| 29 | 66.9 | 7.3 | SSZ-58 |
| 30 | 56.5 | 7.1 | SSZ-58 |
| 31 | 49 | 6.9 | SSZ-58 |
| 32 | 43.5 | 6.7 | SSZ-58 |
| 33 | 39 | 6.6 | SSZ-58 + trace LZ-Y52 |
| 34 | 35.8 | 6.4 | SSZ-58 + trace LZ-Y52 |
| 35 | 33 | 6.26 | SSZ-58 (mostly) + LZ-Y52 |
| 36 | 30.8 | 6.16 | SSZ-58 (mostly) + LZ-Y52 |
| 37 | 26.3 | 5.85 | SSZ-58 (major) LZ-Y52 (minor) |
| 38 | 23.8 | 5.66 | SSZ-58 (major) LZ-Y52 (minor) |
| 39 | 20 | 5.32 | SSZ-58 (major) LZ-Y52 (minor) |

Example 40

Synthesis of All-Silica SSZ-58

A 23 cc. Teflon liner is charged with 6.9 gms. of 0.435M aqueous solution of N-butyl-N-cyclooctylpyrrolidinium hydroxide (3 mmol), 1.2 gms. of 1M NaOH aqueous solution (1.2 mmol NaOH) and 3.9 gm. of deionized water. To the resulting solution, 0.9 gm. of CABOSIL® M-5 amorphous fumed silica (about 14.7 mmol $SiO_2$) is added and the mixture is thoroughly stirred. The resulting mixture is thoroughly stirred and the resulting gel is capped off and placed in a Parr bomb steel reactor and heated in an oven at 160° C. while rotating at 43 rpm. The reaction is monitored by checking the gel's pH, and by looking for crystal formation using SEM at six day intervals. The reaction is completed after heating at the conditions described above for 18 days. The completed reaction mixture appears as a colorless liquid with solids (powder) settled to the bottom of the Teflon liner. The mixture is filtered through a flitted glass funnel. The collected solids are thoroughly washed with water and then rinsed with acetone (10 ml.) to remove any organic residues. The solids are allowed to air-dry overnight and then dried in an oven at 120° C. for one hour. The reaction yields 0.73 gm. of pure SSZ-58.

Example 41

Seeded Synthesis of Borosilicate SSZ-58

A 23 cc Teflon liner is charged with 6.9 gm of 0.435M aqueous solution of N-butyl-N-cyclooctylpyrrolidinium hydroxide (3 mmol), 1.2 gm of 1M aqueous solution of NaOH (1.2 mmol NaOH) and 3.9 gm of de-ionized water. To this mixture, 0.06 gm of sodium borate decahydrate (0.157 mmol of $Na_2B_4O_7.10H_2O$; ~0.315 mmol $B_2O_3$) is added and stirred until completely dissolved. Then, 0.9 gm of CABOSILO® M-5 (~14.7 mmol $SiO_2$) and 0.04 gm of SSZ-58 is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM). The reaction is completed after heating for 5 days at the conditions described above. Once the crystallization is complete, the starting reaction gel turns to a mixture comprising of a clear liquid layer with solids (powder) that settled to the bottom. The mixture is filtered through a fitted-glass fimnel. The collected solids are thoroughly washed with water and, then, rinsed with acetone (10 ml) to remove any organic residues. The solids are allowed to air-dry over night and, then, dried in an oven at 120° C. for one hour. The reaction affords 0.85 gram of a very fine powder. SEM shows the presence of only one crystalline phase. The X-ray pattern identifies the product as SSZ-58.

Example 42

Typical Preparation of Borosilicate SSZ-60 Starting $SiO_2/B_2O_3=46$

In a 23-cc Teflon liner, 5.93 gm of 0.50 M solution (aqueous) of the templating agent N-ethyl-N-(3,3,5-trimethycyclohexyl)pyrrolidinium hydroxide (3 mmol) are mixed with 1.2 gm of 1.0N NaOH (1.2 mmol) and 4.9 gm of de-ionized water. To this mixture, 0.06 gm of sodium borate decahydrate are added and stirred until completely dissolved. To this mixture, 0.9 gm of CABOSIL® M-5 is added. The mixture is thoroughly stirred and the resulting gel is capped off and placed in steel Parr autoclave and heated in an oven at 160° C. while tumbling at 43 rpm. The progress of the reaction is monitored by Scanning Electron Microscopy at intervals of 6 days. Once completed, the reaction mixture (a clear liquid and fine solids settled to the bottom) is filtered through a fritted glass funnel. The collected solid is rinsed with water (1 liter) and air-dried overnight. The solids are further dried in an oven at 120° C. for 2 hours. The reaction yields 0.85 gm of SSZ-60 (determined by X-ray analysis) as a white powder.

SSZ-60 is prepared in a similar manner using N-ethyl-N-(2,4,4-trimethylcyclopentyl)pyrrolidinium cation as the SDA.

Example 43

Synthesis of Beta Zeolite

Using procedures similar to those described in the preceeding examples, zeolite beta is prepared using a N-cyclohexyl-N-benzyl pyrrolidinium cation as the SDA.

Example 44

Synthesis of Boron-ZSM-11

A 23 cc Teflon liner is charged with 5.4 gm of 0.55M aqueous solution of N-butyl-N-cyclopentylpyrrolidinium hydroxide (3 mmol SDA), 1.2 gm of 1M aqueous solution of NaOH (1.2 mmol NaOH) and 5.4 gm of de-ionized water. To this mixture, 0.06 gm of sodium borate decahydrate (0.157 mmol of $Na_2B_4O_7.10H_2O$; about 0.315 mmol $B_2O_3$) are added and stirred until completely dissolved. Then, 0.9 gm of CAB-O-SIL® M-5 amorphous ftuned silica, (about 14.7 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM) at six day intervals. Once the reaction is complete (after heating for 12 days at the conditions described above), the resulting mixture, comprising a clear liquid layer and powdery solids settled to the bottom of the Teflon liner, is filtered through a fritted-glass funnel. The collected solids are thoroughly washed with water and then rinsed with acetone (~10 ml) to remove any organic residues. The solids are allowed to air-dry over night and then dried in an oven at 120° C. for 1 hour. The product is identified by XRD as ZSM-11.

Example 45

Synthesis of Boron-ZSM-12

A 23 cc Teflon liner is charged with 5.9 gm of 0.51M aqueous solution of N-methyl-N-cyclohexylpyrrolidinium hydroxide (3 mmol SDA), 1.2 gm of 1M aqueous solution of NaOH (1.2 mmol NaOH) and 4.9 gm of de-ionized water. To this mixture, 0.06 gm of sodium borate decahydrate (0.157 mmol of $Na_2B_4O_7.10H_2O$; about 0.315 mmol $B_2O_3$) are added and stirred until completely dissolved. Then, 0.9 gm of CAB-O-SIL® M-5 amorphous fumed silica, (about 14.7 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM) at six day intervals. The reaction is completed after heating for 6 days at the conditions described above. Then, the reaction mixture, comprising a clear liquid layer with solids (powder) settled to the bottom of the Teflon liner, is filtered through a fritted-glass funnel. The collected solids are thoroughly washed with water and then rinsed with acetone (10 ml) to remove any organic residues. The solids are allowed to air-dry over night and then dried in an oven at 120° C. for 1 hour. The reaction affords 0.88 gram of ZSM-12.

ZSM-12 is also prepared using N-cyclopentyl-N-methylpyrrolidinium cation, N-cyclohexyl-N-ethylpyrrolidinium cation, N-cyclohexyl-N-propylpyrrolidinium cation, N-cycloheptyl-N-methylpyrrolidinium cation, N-cycloheptyl-N-ethylpyrrolidinium cation, N-butyl-N-cycloheptyl pyrrolidinium cation, N-cyclooctyl-N-methylpyrrolidinium cation, or N-cyclooctyl-N-ethylpyrrolidinium cation as the SDA.

Example 46

Synthesis of Aluminum-SSZ-37

A 23 cc Teflon liner is charged with 4.9 gm of 0.46M aqueous solution of N-cyclopentyl-N-ethylpyrrolidinium hydroxide (2.25 mmol SDA), 1.5 gm of 1M aqueous solution of NaOH (1.5 mmol NaOH) and 1 gm of de-ionized water. To this mixture, 0.25 gm of Union Carbide's LZ-Y52 zeolite (SiO2/Al2O3=5) are added and stirred in. Then, 0.8 gm of CAB-O-SIL® M-5 amorphous fumed silica, (about 13 mmol $SiO_2$) is added to the solution and the mixture is thoroughly stirred. The resulting gel is capped off and placed in a Parr bomb steel reactor and heated in an oven at 160° C. while rotating at 43 rpm. The reaction is monitored by checking the gel's pH, and by looking for crystal formation using Scanning Electron Microscopy (SEM) at six day intervals. The reaction is completed after heating for 12 days at the conditions described above. Then, the reaction mixture, comprising of a clear liquid layer and solids (powder) settled to the bottom of the Teflon liner, is filtered through a fritted-glass funnel. The collected solids are thoroughly washed with water and then rinsed with minimal amount of acetone (about 10 ml) to remove any organic residues. The solids are allowed to air-dry over night and then dried in an oven at 120° C. for 1 hour. The reaction affords 0.82 gram of SSZ-37.

Example E

Synthesis of N-Cyclohexyl-N-(2-methylpropyl) pyrrolidinium Cation

The parent amine N-cyclohexylpyrrolidine is synthesized as described in Example A above.
Quaternization (synthesis of N-cyclohexyl-N-(2-methylpropyl)pyrrolidinium iodide In a 1-liter three-neck reaction flask equipped with a mechanical stirrer and reflux condenser, 20 gm (0 13 mol) of N-cyclohexylpyrrolidine are dissolved in 250 ml methanol (ACS reagent). To this solution, 20 gm (0.2 mol) of $KHCO_3$ and 48 gm (0.26 mol) of 2-methyl-1-iodopropane are added, sequentially. The resulting mixture is stirred at room temperature for 36 hrs, but the reaction goes very sluggishly. Then, the reaction is refluxed over the weekend (approximately 72 hours). Then, the reaction mixture is concentrated on a rotary evaporator under reduced to give a mixture of solids. The obtained solids are washed three times with chloroform (300 ml each), and all the chloroform washes are combined and concentrated on a rotary evaporator under reduced pressure to give 31 gm of a tan colored solid material. $^1$H and $^{13}$C NMR spectra are ideal for the desired N-cyclohexyl-N-(2-methylpropyl)pyrrolidinium iodide salt. The product is then recrystallized by dissolving in a minimal amount of isopropyl alcohol and precipitated by adding ethyl ether. The crystallization process affords 27 gm of the pure product.

Ion Exchange: The ion exchange is done in a similar fashion to the ion exchange procedure described above in Example A using BIO RAD® AG1-X8 ion exchange resin (hydroxide form).

Example 47

Preparation of Borosilicate SSZ-55

Starting $SiO_2/B_2O_3=35$

To a mixture of N-cyclohexyl-N-(2-methylpropyl) pyrrolidiniun hydroxide (3 mmol), 1.2 mmol NaOH (1.2 gm of 1 N aqueous solution) and 3.3 gm of water in a 23 cc Teflon cup, a 0.08 gm of sodium borate decahydrate ($Na_2B_4O_7\cdot10\ H_2O$) are added and stirred until completely dissolved. To this solution, 0.9 gm of CAB-O-SIL® M-5 amorphous fumed silica (about 14.7 mmol $SiO_2$ are added and the mixture is thoroughly stirred. The resulting gel is capped off and placed in a Parr reactor and heated in an oven at 160° C. while rotating at 43 rpm.

The reaction is monitored by checking the gel's pH, and by looking for crystal formation using Scanning Electron Microscopy (SEM) every six days. The reaction is completed after heating at the temperature described above (while rotating at 43 rpm)) for 12 days. The reaction mixture appears as a colorless liquid with fine white solid settled at the bottom of the Teflon liner. The mixture is filtered through a fritted-glass funnel, and the obtained white solids are washed several times with water (a total of 1 liter) and, then, are allowed to air-dry over night to yield 0.84 gram of a fine white powder. SEM indicates the presence of only one crystalline phase. Analysis by XRD shows the product to be SSZ-55.

SSZ-55 is prepared in a similar manner using in turn a N-propyl-N-cyclohexyl pyrrolidinium cation and N-cyclopentyl-N-(2-methylpropyl)pyrrolidinium cation as the SDA.

What is claimed is:

1. A process for preparing a medium pore size zeolite which comprises:

(a) preparing an aqueous solution from (1) sources of an alkali metal oxide, alkaline earth metal oxide or mixtures thereof; (2) sources of an oxide selected from the oxides of aluminum, iron, gallium, indium, titanium, vanadium or mixtures thereof; (3) sources of an oxide selected from oxides of silicon, germanium or mixtures thereof; and (4) at least one pyrrolidinium cation capable of forming the zeolite and having the following formula:

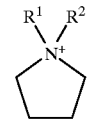

(I)

where $R^1$ is $C_1$–$C_4$ alkyl or benzyl, and $R^2$ is $C_5$–$C_8$ cycloalkyl, or alkylated $C_5$–$C_8$ cycloalkyl;

(b) maintaining the aqueous solution under conditions sufficient to form crystals of the zeolite; and (c) recovering the crystals of the zeolite.

2. The process of claim 1 wherein said aqueous solution comprises, in terms of mole ratios, the following:

$YO_2/W_aO_b$ 20–∞
$OH^-/YO_2$ 0.10–0.50
$Q/YO_2$ 0.05–0.50
$M_{2/n}/YO_2$ 0.02–0.40
$H_2O/YO_2$ 10–100 where Y is silicon, germanium or mixtures thereof; W is aluminum, boron, iron, gallium, indium, titanium, vanadium or mixtures thereof; a is 1 or 2, and b is 2 when a is 1 and b is 3 when a is 2; Q is at least one pyrrolidinium cation capable of forming the zeolite and having formula (I); M is an alkali metal, alkaline earth metal or mixtures thereof; and n is the valence of M.

3. The process of claim 1 wherein the pyrrolidinium cation is selected from the group consisting of cations having the following structures:

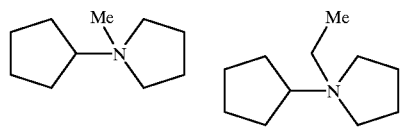

-continued

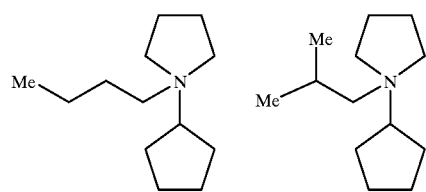
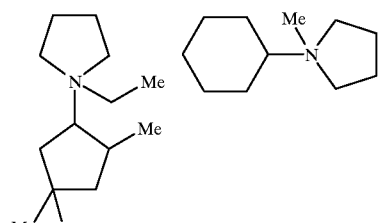
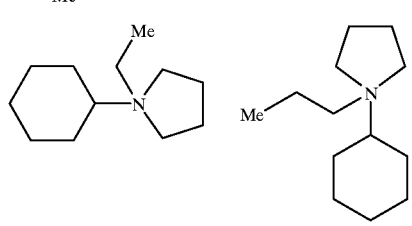
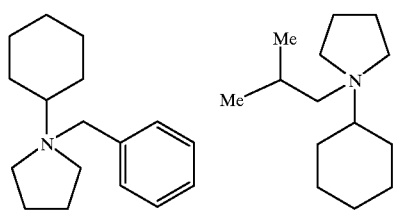
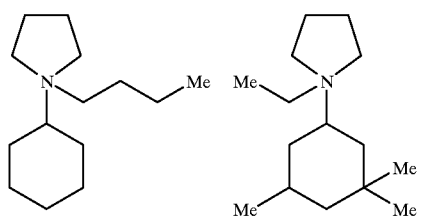
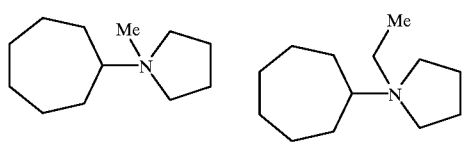
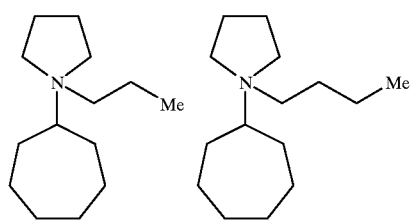
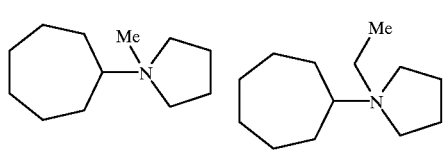

-continued

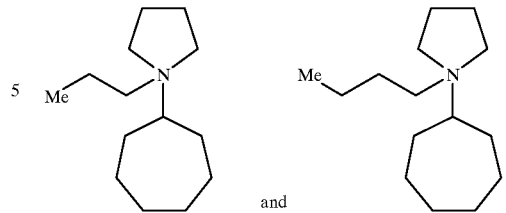

and

4. The process of claim 1 wherein the pyrrolidinium cation has the following structure:

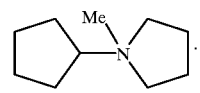

5. The process of claim 1 wherein the pyrrolidinium cation has the following structure:

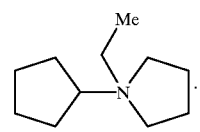

6. The process of claim 1 wherein the pyrrolidinium cation has the following structure:

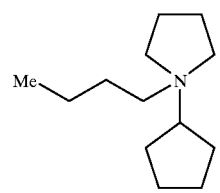

7. The process of claim 1 wherein the pyrrolidinium cation has the following structure:

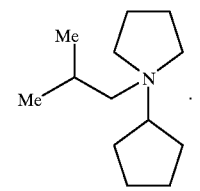

8. The process of claim 1 wherein the pyrrolidinium cation has the following structure:

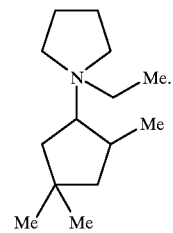

9. The process of claim 1 wherein the pyrrolidinium cation has the following structure:

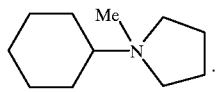

10. The process of claim 1 wherein the pyrrolidinium cation has the following structure:

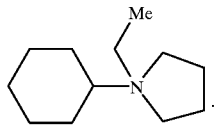

11. The process of claim 1 wherein the pyrrolidinium cation has the following structure:

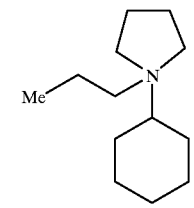

12. The process of claim 1 wherein the pyrrolidinium cation has the following structure:

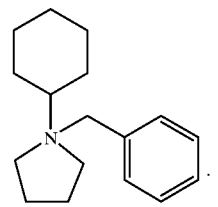

13. The process of claim 1 wherein the pyrrolidinium cation has the following structure:

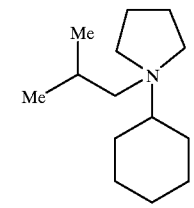

14. The process of claim 1 wherein the pyrrolidinium cation has the following structure:

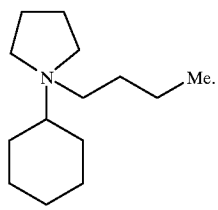

15. The process of claim 1 wherein the pyrrolidinium cation has the following structure:

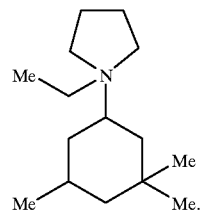

16. The process of claim 1 wherein the pyrrolidinium cation has the following structure:

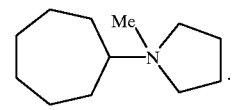

17. The process of claim 1 wherein the pyrrolidinium cation has the following structure:

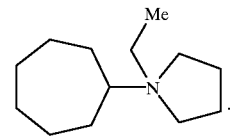

18. The process of claim 1 wherein the pyrrolidinium cation has the following structure:

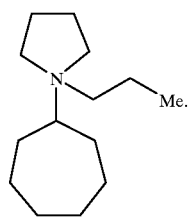

19. The process of claim 1 wherein the pyrrolidinium cation has the following structure:

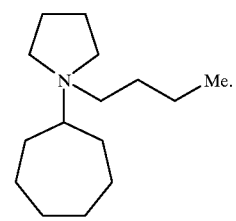

20. The process of claim 1 wherein the pyrrolidinium cation has the following structure:

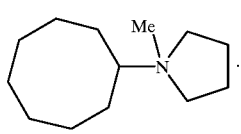

21. The process of claim 1 wherein the pyrrolidinium cation has the following structure:

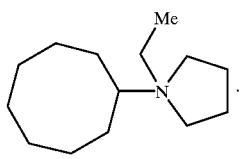

22. The process of claim 1 wherein the pyrrolidinium cation has the following structure:

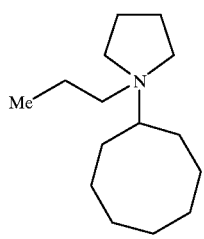

23. The process of claim 1 wherein the pyrrolidinium cation has the following structure:

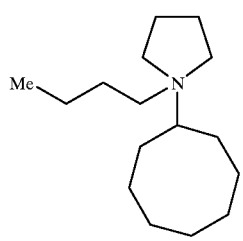

24. The process of claim 1 further comprising replacing the alkali metal cations, alkaline earth metal cations, or both of the recovered zeolite, at least in part, by ion exchange with a cation or mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

25. The process of claim 24 wherein said replacing cation is hydrogen or a hydrogen precursor.

26. The process of claim 1 wherein the zeolite is ZSM-11 and the pyrrolidinium cation has the formula

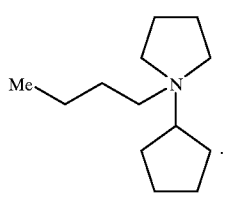

27. The process of claim 1 wherein the zeolite is ZSM-12 and the pyrrolidinium cation has the formula

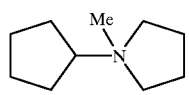 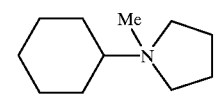

-continued

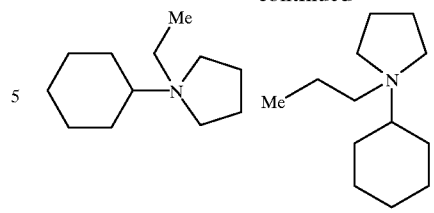

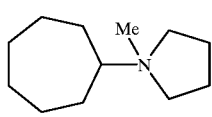

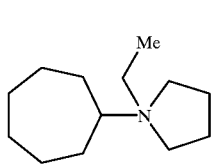

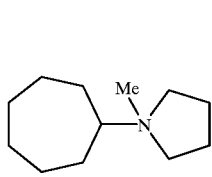

 or .

28. The process of claim 1 wherein the zeolite is zeolite beta and the pyrrolidinium cation has the formula

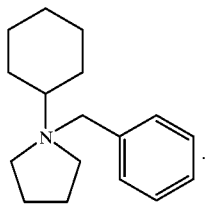

29. The process of claim 1 wherein the zeolite is SSZ-37 and the pyrrolidinium cation has the formula

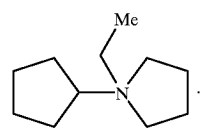

30. The process of claim 1 wherein the zeolite is SSZ-55 and the pyrrolidinium cation has the formula

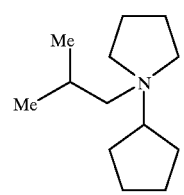

-continued

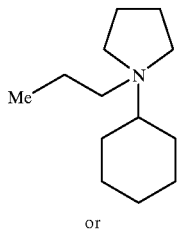

or

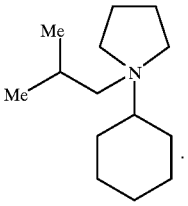

31. A zeolite composition, as-synthesized and in the anhydrous state, whose general formula, in terms of mole ratios, is as follows:

$YO_2/W_cO_d \geq 20$ $Q/YO_2$ 0.02–0.10

$M_{2/n}/YO_2$ 0.01–0.10 wherein Y is silicon, germanium or a mixture thereof; W is aluminum, boron gallium, indium, iron, titanium, vanadium or mixtures thereof; c is 1 or 2; d is 2 when c is 1 or d is 3 or 5 when c is 2; Q is at least one pyrrolidinium cation capable of forming the zeolite and having the formula

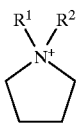 (I)

where $R^1$ is $C_1$–$C_4$ alkyl or benzyl, and $R^2$ is $C_5$–$C_8$ cycloalkyl, or alkylated $C_5$–$C_8$ cycloalkyl; M is alkali metal cation, alkaline earth metal cations or mixtures thereof, n is the valence of M.

32. The composition of claim 31 wherein Q is selected from the group consisting of cations having the following structures:

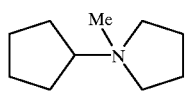 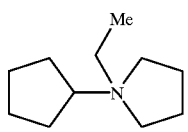

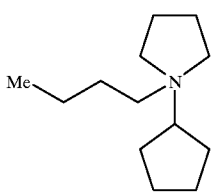 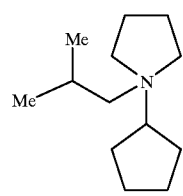

-continued

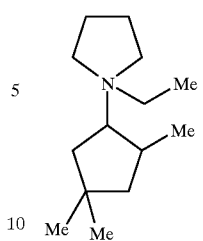 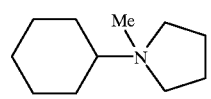

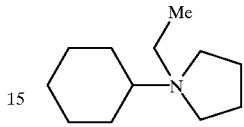

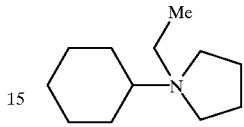 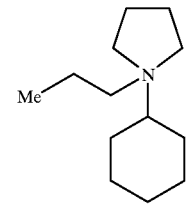

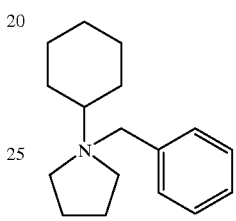 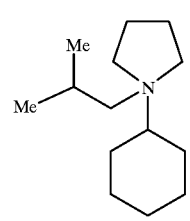

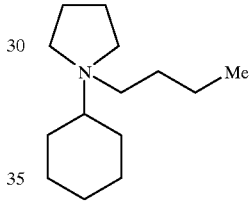 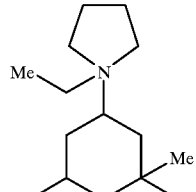

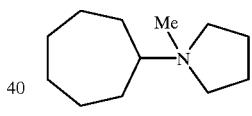 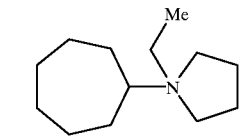

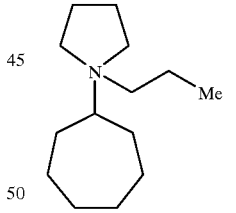 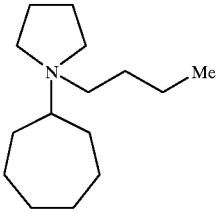

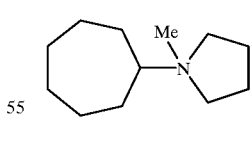 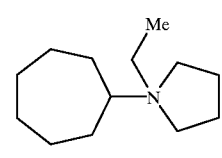

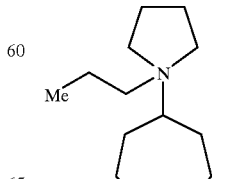 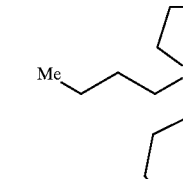

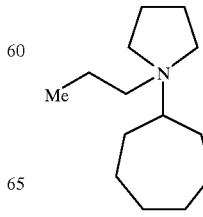 and 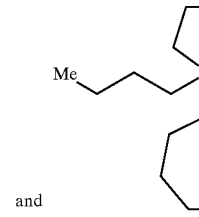.

33. The composition of claim 31 wherein Q has the following structure:

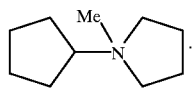

34. The composition of claim 31 wherein Q has the following structure:

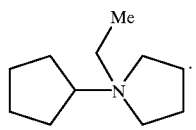

35. The composition of claim 31 wherein Q has the following structure:

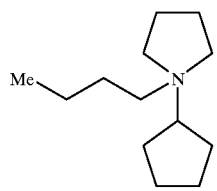

36. The composition of claim 31 wherein Q has the following structure:

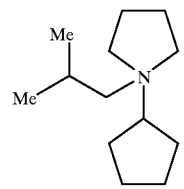

37. The composition of claim 31 wherein Q has the following structure:

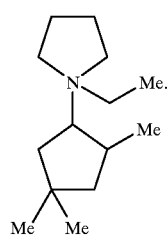

38. The composition of claim 31 wherein Q has the following structure:

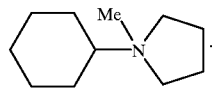

39. The composition of claim 31 wherein Q has the following structure:

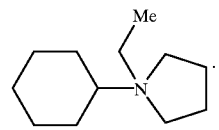

40. The composition of claim 31 wherein Q has the following structure:

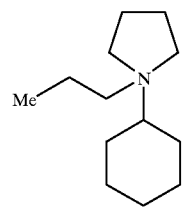

41. The composition of claim 31 wherein Q has the following structure:

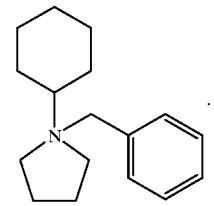

42. The composition of claim 31 wherein Q has the following structure:

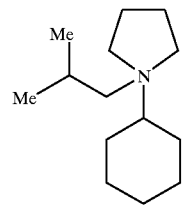

43. The composition of claim 31 wherein Q has the following structure:

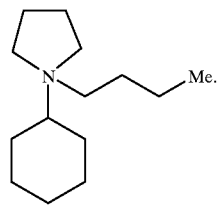

44. The composition of claim 31 wherein Q has the following structure:

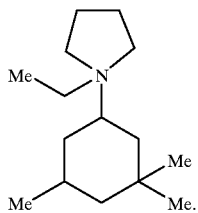

45. The composition of claim 31 wherein Q has the following structure:

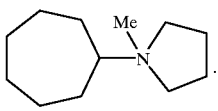

46. The composition of claim 31 wherein has the following structure:

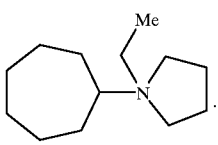

47. The composition of claim 31 wherein Q has the following structure:

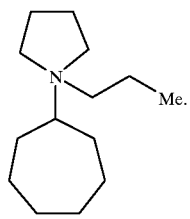

48. The composition of claim 31 wherein Q has the following structure:

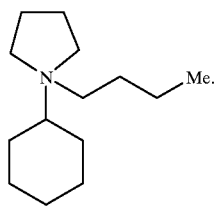

49. The composition of claim 31 wherein Q has the following structure:

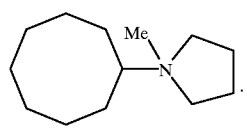

50. The composition of claim 31 wherein Q has the following structure:

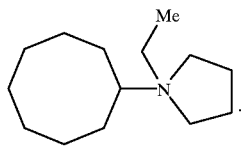

51. The composition of claim 31 wherein Q has the following structure:

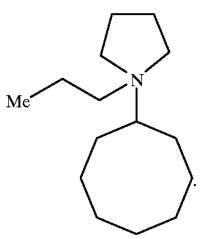

52. The composition of claim 31 wherein Q has the following structure:

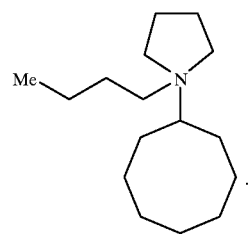

53. The composition of claim 31 wherein the zeolite is ZSM-11 and the pyrrolidinium cation has the formula

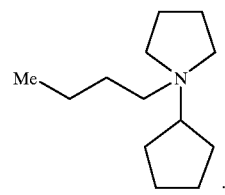

54. The composition of claim 31 wherein the zeolite is ZSM-12 and the pyrrolidinium cation has the formula

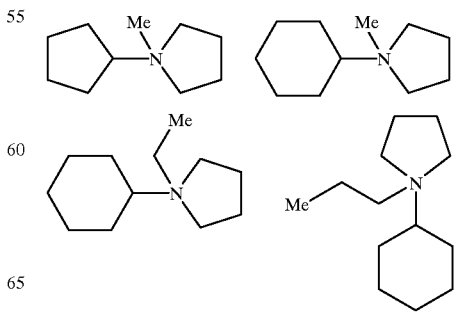

-continued
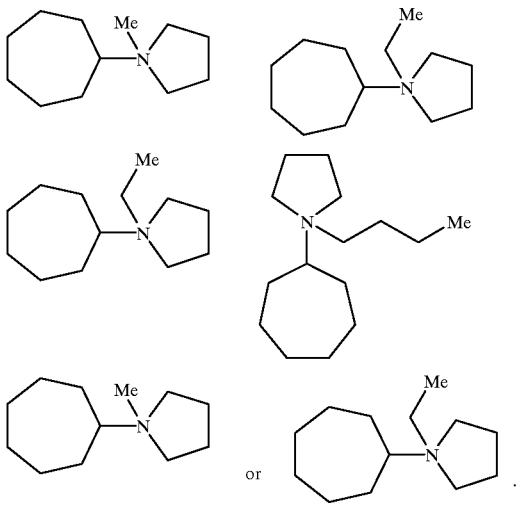
55. The composition of claim 31 wherein the zeolite is zeolite beta and the pyrrolidinium cation has the formula
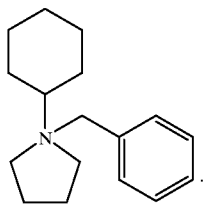
56. The composition of claim 31 wherein the zeolite is SSZ-37 and the pyrrolidinium cation has the formula
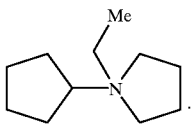
57. The composition of claim 31 wherein the zeolite is SSZ-55 and the pyrrolidinium cation has the formula
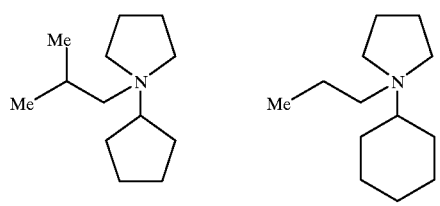
or
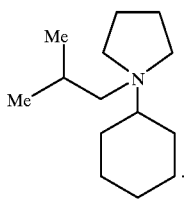
* * * * *